United States Patent
Barrall et al.

(10) Patent No.: US 12,416,624 B2
(45) Date of Patent: Sep. 16, 2025

(54) FARADAIC SYSTEMS AND METHODS FOR SELF-LIMITING PROTEIN PORE INSERTION IN AMEMBRANE

(71) Applicant: Roche Sequencing Solutions, Inc., Pleasanton, CA (US)

(72) Inventors: Geoffrey Barrall, San Diego, CA (US); Eric Takeshi Harada, San Jose, CA (US); Jason David Komadina, Livermore, CA (US); J. William Maney, Jr., Emerald Hills, CA (US); Charlotte Yang, Vancouver, WA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 391 days.

(21) Appl. No.: 18/064,037

(22) Filed: Dec. 9, 2022

(65) Prior Publication Data
US 2023/0105456 A1   Apr. 6, 2023

Related U.S. Application Data

(63) Continuation of application No. PCT/EP2021/065252, filed on Jun. 8, 2021.
(Continued)

(51) Int. Cl.
*G01N 33/487* (2006.01)
*C12Q 1/6869* (2018.01)

(52) U.S. Cl.
CPC ..... *G01N 33/48721* (2013.01); *C12Q 1/6869* (2013.01); *C12Q 2565/607* (2013.01); *C12Q 2565/631* (2013.01)

(58) Field of Classification Search
CPC combination set(s) only.
See application file for complete search history.

(56) References Cited

U.S. PATENT DOCUMENTS

| 10,102,338 B2 | 10/2018 | Fernandez-Gomez |
| 10,393,700 B2 | 8/2019 | Chen |

(Continued)

FOREIGN PATENT DOCUMENTS

| EP | 3545300 A1 | 10/2019 |
| JP | 2018535396 A | 11/2018 |

(Continued)

OTHER PUBLICATIONS

International Search Report and Written Opinion Issued Oct. 6, 2021 for PCT/EP2021/065252 Filed Jun. 8, 2021.

*Primary Examiner* — J. Christopher Ball
(74) *Attorney, Agent, or Firm* — FisherBroyles, LLP; Jason M. Pass

(57) ABSTRACT

Systems and methods for inserting a single pore into a membrane under faradaic conditions are described herein. A stepped or ramped voltage waveform can be applied across the membranes of the cells of an array, where the voltage waveform starts at first voltage and increases in magnitude over a period of time to a second voltage. The voltage waveform has a polarity that maintains a first species of a redox couple in its current oxidation state. The first voltage is selected to be low enough to reduce the risk of damaging the membrane, while the rate of voltage increase is selected to provide sufficient time for the pores to insert into the membranes. Once a pore is inserted into the membrane, the voltage across the membrane rapidly drops, thereby reducing the risk of damaging the membrane even if the applied voltage between the electrodes is further increased.

31 Claims, 10 Drawing Sheets

Related U.S. Application Data

(60) Provisional application No. 62/705,097, filed on Jun. 10, 2020.

(56) References Cited

U.S. PATENT DOCUMENTS

| 2011/0193570 A1* | 8/2011 | Chen | G01N 33/48721 |
| | | | 324/654 |
| 2017/0089857 A1* | 3/2017 | Maney | B82Y 35/00 |
| 2020/0179920 A1 | 6/2020 | Garalde | |

FOREIGN PATENT DOCUMENTS

| WO | 2017050721 A1 | 3/2017 |
| WO | 2018096348 A1 | 5/2018 |
| WO | 2020109800 A1 | 6/2020 |

* cited by examiner

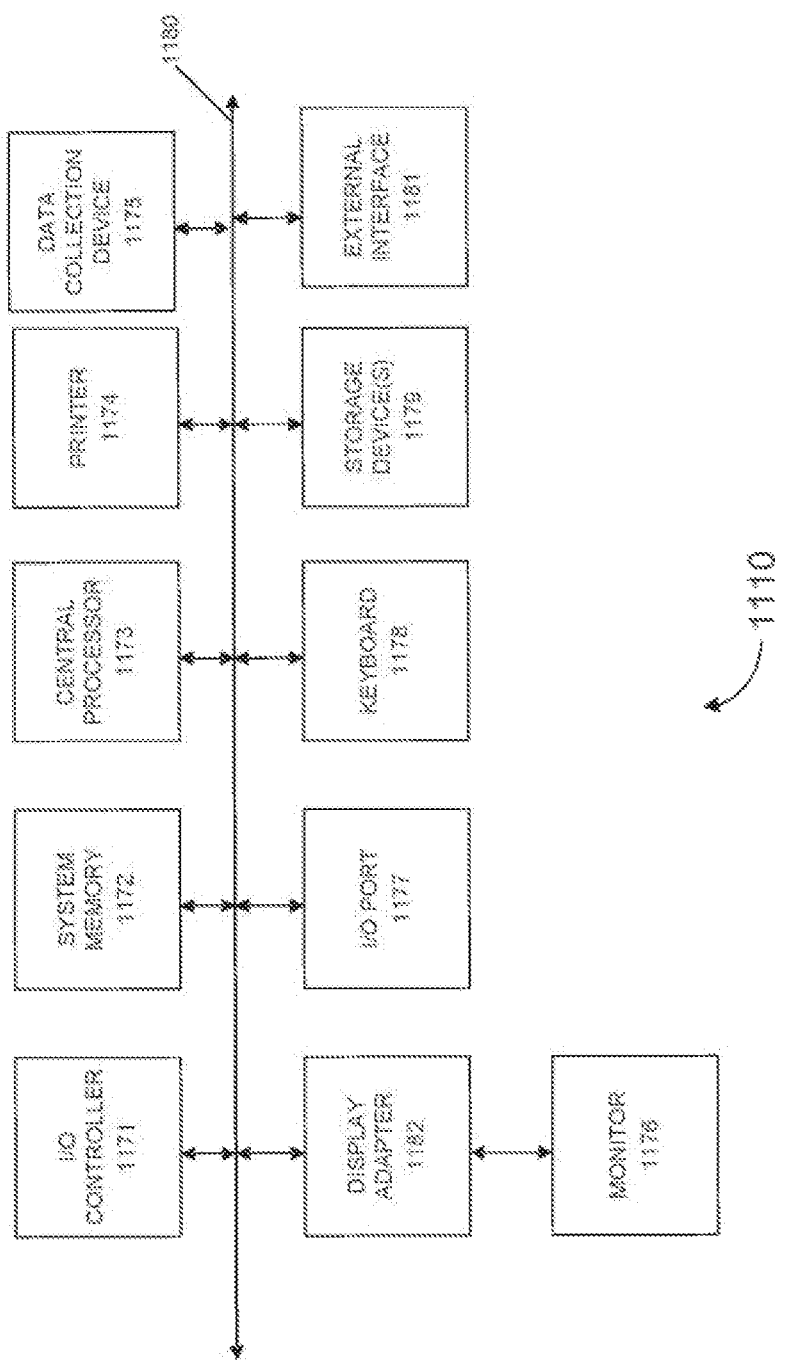

FARADAIC SYSTEMS AND METHODS FOR SELF-LIMITING PROTEIN PORE INSERTION IN A MEMBRANE

CROSS REFERENCE TO RELATED APPLICATIONS

This application is a continuation of International Patent Application No. PCT/EP2021/065252, filed on Jun. 8, 2021, which claims priority to U.S. Provisional Application No. 62/705,097, filed Jun. 10, 2020, each of which is herein incorporated by reference in its entirety for all purposes.

This application may be related to International Patent Application No. PCT/EP2019/084581, filed Dec. 11, 2019, which claims priority to U.S. Provisional Application No. 62/777,976, filed Dec. 11, 2018, each of which is herein incorporated by reference in its entirety for all purposes.

INCORPORATION BY REFERENCE

All publications and patent applications mentioned in this specification are herein incorporated by reference to the same extent as if each individual publication or patent application was specifically and individually indicated to be incorporated by reference.

BACKGROUND

A nanopore based sequencing chip is an analytical tool that can be used for DNA sequencing. These devices can incorporate a large number of sensor cells configured as an array. For example, a sequencing chip can include an array of one million cells, with, for example, 1000 rows by 1000 columns of cells. Each cell of the array can include a membrane and a protein pore having a pore size on the order of one nanometer in internal diameter. Such nanopores have been shown to be effective in rapid nucleotide sequencing.

When a voltage potential is applied across a nanopore immersed in a conducting fluid, a small ion current attributed to the conduction of ions across the nanopore can exist. The size of the current is sensitive to the pore size and the type of molecule positioned within the nanopore. The molecule can be a particular tag attached to a particular nucleotide, thereby allowing detection of a nucleotide at a particular position of a nucleic acid. A voltage or other signal in a circuit including the nanopore can be measured (e.g., at an integrating capacitor) as a way of measuring the resistance of the molecule, thereby allowing detection of which molecule is in the nanopore.

For the sequencing chip to work properly, generally only one pore should be inserted the membrane for a given cell. If multiple pores are inserted into a single membrane, the electrical signature generated by nucleotides passing simultaneously through the multiple pores will be much harder to interpret.

Application of voltage across the membrane during the pore insertion step may facilitate the process of pore insertion, possibly by reducing the stability of the membrane and allowing the pore to more easily insert itself into the membrane. However, application of too large a voltage across the membrane can cause extensive disruption of the membrane that renders the cell unusable.

Therefore, it would be advantageous to provide a system and method for reliably inserting a single pore into the membrane while reducing the risk of excessively damaging the membrane.

BRIEF SUMMARY

Various embodiments provide techniques and systems related to the insertion of a single pore into a membrane in a cell of a nanopore based sequencing chip. In some embodiments, the insertion of a pore into the membrane reduces the likelihood of insertion of an additional pore into the membrane.

Other embodiments are directed to systems and computer readable media associated with methods described herein.

In some embodiments, a method of forming an array of nanopore sensor cells is provided. The method includes introducing a nanopore proximate to a cell, the cell having a working electrode and a membrane sealing the cell, wherein the working electrode is powered by an AC coupled power source; applying a voltage waveform across the membrane of the cell, wherein the voltage waveform starts at first voltage and increases in magnitude over a period of time to a second voltage; and inserting the nanopore into the membrane during the step of applying the voltage waveform.

In some embodiments, the first voltage is between about 0 and 100 mV and the second voltage is between about 100 to 2000 mV.

In some embodiments, the working electrode is a capacitive electrode.

In some embodiments, the voltage waveform comprises a plurality of incremental steps between the first voltage and the second voltage.

In some embodiments, the plurality of incremental steps are incremented by about 1 to 100 mV.

In some embodiments, the plurality of incremental steps are incremented by about 1 to 25 mV.

In some embodiments, each incremental step has a duration between about 0.1 to 60 seconds.

In some embodiments, the duration of the incremental steps is variable.

In some embodiments, the duration of the incremental steps at lower voltages is greater than the duration of the of incremental steps at the higher voltages.

In some embodiments, the duration of the incremental steps is constant.

In some embodiments, the voltage waveform comprises a ramp between the first voltage and the second voltage.

In some embodiments, the ramp is between about 0.1 to 2.0 V per minute.

In some embodiments, the ramp has a constant slope.

In some embodiments, the ramp has a variable slope.

In some embodiments, the ramp has a slope at lower voltages that is less than the slope at higher voltages.

In some embodiments, the step of applying the voltage waveform is applied to an unthinned membrane.

In some embodiments, the method further includes thinning the unthinned membrane with the applied voltage waveform.

In some embodiments, a system for sequencing a molecule is provided. The system includes an array of cells on a substrate, each cell having a working electrode and an opening configured to be sealed by a membrane, wherein the working electrode is powered by an AC coupled power source; a counter electrode; a power source, wherein the power source is AC coupled to each working electrode; a controller programmed to: deliver a voltage waveform to the cell using the working electrode and the counter electrode, wherein the voltage waveform starts at first voltage and increases in magnitude over a period of time to a second voltage.

In some embodiments, the working electrode is a capacitive electrode.

In some embodiments, the voltage waveform comprises a plurality of incremental steps between the first voltage and the second voltage.

In some embodiments, the voltage waveform comprises a ramp between the first voltage and the second voltage.

In some embodiments, the controller is further programmed to deliver the voltage waveform to an unthinned membrane.

In some embodiments, a method of forming an array of nanopore sensor cells is provided. The method can include introducing a nanopore proximate to a cell, the cell having a working electrode and a membrane sealing the cell, wherein the working electrode is powered by an electrically coupled power source; applying a voltage waveform across the membrane of the cell, wherein the voltage waveform starts at first voltage and increases in magnitude over a period of time to a second voltage, wherein the voltage waveform includes an AC modulation component, the AC modulation component configured to allow electrical measurements to be taken through the working electrode while the voltage waveform is applied across the membrane of the cell; and inserting the nanopore into the membrane during the step of applying the voltage waveform.

In some embodiments, the AC modulation component has an amplitude of less than 100 mV. In some embodiments, the AC modulation component has a frequency between 10 Hz and 1000 Hz.

In some embodiments, a method of forming a membrane covered cell is provided. The method can include flowing a membrane forming material over a cell, the cell having a working electrode, wherein the working electrode is powered by an electrically coupled power source; disposing a layer of membrane forming material over the cell; applying a voltage waveform across the layer of membrane forming material with the working electrode and a counter electrode on an opposing side of the layer of membrane forming material, wherein the voltage waveform includes an AC modulation component, the AC modulation component configured to allow electrical measurements to be taken through the working electrode while the voltage waveform is applied across the layer of membrane forming material; and thinning the layer of membrane forming material into a membrane, the membrane configured to receive a nanopore.

In some embodiments, the AC modulation component has an amplitude of less than 100 mV. In some embodiments, the AC modulation component has a frequency between 10 Hz and 1000 Hz.

A better understanding of the nature and advantages of embodiments of the present invention can be gained with reference to the following detailed description and the accompanying drawings.

In some embodiments, a method of forming an array of nanopore sensor cells is provided. The method can include introducing a nanopore proximate to a cell in a solution containing a first species of a redox couple but not a second species of the redox couple, the cell having a working electrode and a membrane sealing the cell, wherein the working electrode is powered by an electrically coupled power source; applying a voltage waveform across the membrane of the cell, wherein the voltage waveform starts at first voltage and increases in magnitude over a period of time to a second voltage, wherein the voltage waveform has a polarity that maintains the first species of the redox couple in its current oxidation state; and inserting the nanopore into the membrane during the step of applying the voltage waveform.

In some embodiments, the redox couple is water soluble. In some embodiments, the redox couple is ferricyanide and ferrocyanide.

In some embodiments, the method further includes applying a second voltage waveform having a polarity that oxidizes or reduces the first species to the second species.

In some embodiments, the method further includes threading a molecule through the pore; and applying a sequencing voltage to sequence the molecule under faradaic conditions.

In some embodiments, a system for sequencing a molecule is provided. The system can include an array of cells on a substrate, each cell having a working electrode and an opening configured to be sealed by a membrane having a nanopore; a counter electrode; a power source, wherein the power source is electrically coupled to each working electrode; a controller programmed to: deliver a voltage waveform to the cell using the working electrode and the counter electrode, wherein the voltage waveform starts at first voltage and increases in magnitude over a period of time to a second voltage, wherein the voltage waveform has a polarity that maintains a first species of a redox couple in its current oxidation state.

In some embodiments, the working electrode is configured to selectively operate as both a capacitively-coupled electrode and a resistively couple electrode.

In some embodiments, the controller is further programmed to deliver a second voltage waveform having a polarity that oxidizes or reduces the first species to the second species.

In some embodiments, the system further includes a solution containing the first species of the redox couple but not a second species of the redox couple, where the solution is configured to be disposed in the cells of the array. In some embodiments, the redox couple is water soluble. In some embodiments, the redox couple is ferricyanide and ferrocyanide.

In some embodiments, the controller is further programmed to apply a voltage to thread a molecule through the pore; and apply a sequencing voltage to sequence the molecule under faradaic conditions.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 11 is a computer system, according to certain aspects of the present disclosure.

TERMS

Figure 1:
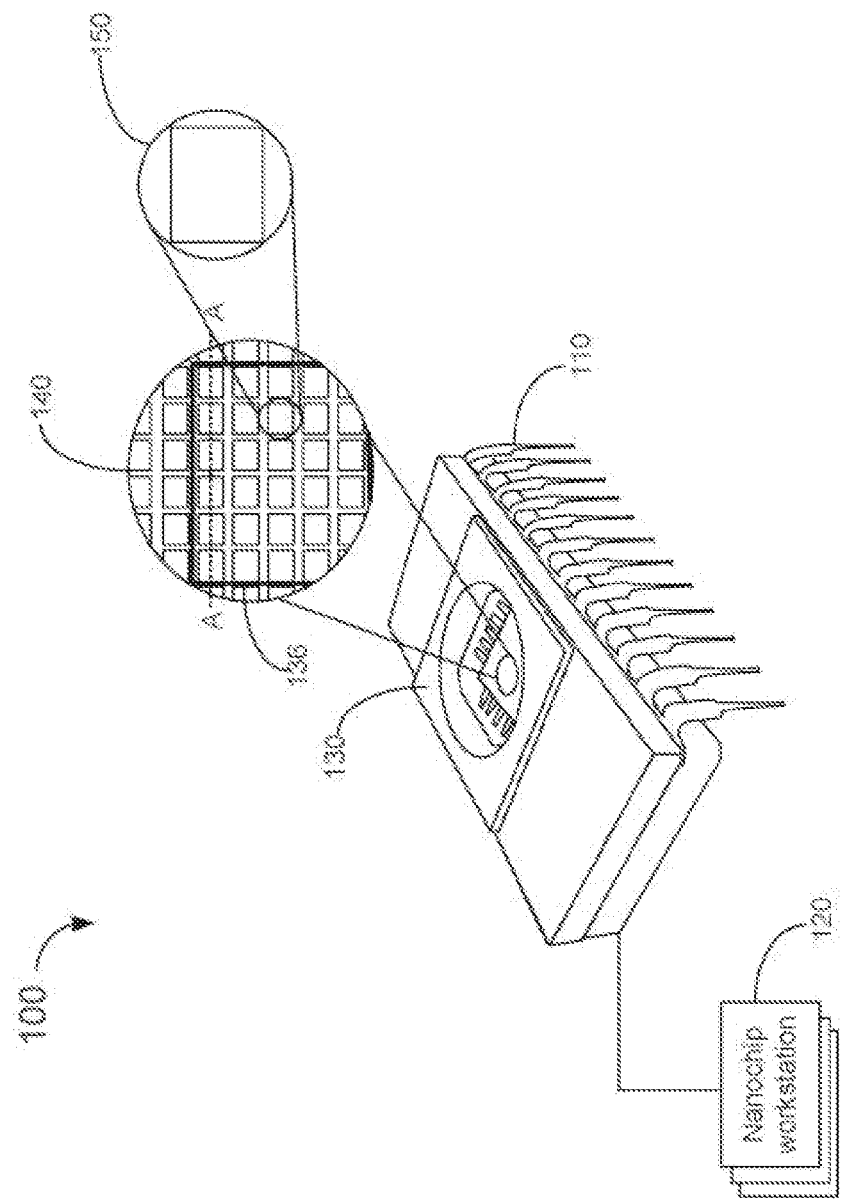
FIG. 1 is a top view of an embodiment of a nanopore sensor chip having an array of nanopore cells.

Unless defined otherwise, technical and scientific terms used herein have the same meaning as commonly understood by a person of ordinary skill in the art. Methods, devices, and materials similar or equivalent to those described herein can be used in the practice of disclosed techniques. The following terms are provided to facilitate understanding of certain terms used frequently and are not meant to limit the scope of the present disclosure. Abbreviations used herein have their conventional meaning within the chemical and biological arts.

A "nanopore" refers to a pore, channel or passage formed or otherwise provided in a membrane. A membrane can be an organic membrane, such as a lipid bilayer, or a synthetic membrane, such as a membrane formed of a polymeric material. The nanopore can be disposed adjacent or in proximity to a sensing circuit or an electrode coupled to a sensing circuit, such as, for example, a complementary metal oxide semiconductor (CMOS) or field effect transistor (FET) circuit. In some examples, a nanopore has a characteristic width or diameter on the order of 0.1 nanometers (nm) to about 1000 nm. In some implementations, a nanopore may be a protein.

A "nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidites, methyl phosphonates, chiral-methyl phosphonates, 2-O-methyl ribonucleotides, and peptide-nucleic acids (PNAs). Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions can be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid can be used interchangeably with gene, cDNA, mRNA, oligonucleotide, and polynucleotide.

The term "nucleotide," in addition to referring to the naturally occurring ribonucleotide or deoxyribonucleotide monomers, can be understood to refer to related structural variants thereof, including derivatives and analogs, that are functionally equivalent with respect to the particular context in which the nucleotide is being used (e.g., hybridization to a complementary base), unless the context clearly indicates otherwise.

The term "tag" refers to a detectable moiety that can be atoms or molecules, or a collection of atoms or molecules. A tag can provide an optical, electrochemical, magnetic, or electrostatic (e.g., inductive, capacitive) signature, which signature can be detected with the aid of a nanopore. Typically, when a nucleotide is attached to the tag it is called a "Tagged Nucleotide." The tag can be attached to the nucleotide via the phosphate moiety.

The term "template" refers to a single stranded nucleic acid molecule that is copied into a complementary strand of DNA nucleotides for DNA synthesis. In some cases, a template can refer to the sequence of DNA that is copied during the synthesis of mRNA.

The term "primer" refers to a short nucleic acid sequence that provides a starting point for DNA synthesis. Enzymes that catalyze the DNA synthesis, such as DNA polymerases, can add new nucleotides to a primer for DNA replication.

A "polymerase" refers to an enzyme that performs template-directed synthesis of polynucleotides. The term encompasses both a full length polypeptide and a domain that has polymerase activity. DNA polymerases are well-known to those skilled in the art, and include but are not limited to DNA polymerases isolated or derived from *Pyrococcus furiosus, Thermococcus litoralis*, and *Thermotoga maritime*, or modified versions thereof. They include both DNA-dependent polymerases and RNA-dependent polymerases such as reverse transcriptase. At least five families of DNA-dependent DNA polymerases are known, although most fall into families A, B and C. There is little or no sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found—DNA polymerases I (family A), II (family B), and III (family C). In eukaryotic cells, three different family B polymerases—DNA polymerases α, δ, and ε—are implicated in nuclear replication, and a family A polymerase—polymerase γ—is used for mitochondrial DNA replication. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

The term "bright period" generally refers to the time period when a tag of a tagged nucleotide is forced into a nanopore by an electric field applied through an AC signal. The term "dark period" generally refers to the time period when a tag of a tagged nucleotide is pushed out of the nanopore by the electric field applied through the AC signal. An AC cycle can include the bright period and the dark period. In different embodiments, the polarity of the voltage signal applied to a nanopore cell to put the nanopore cell into the bright period (or the dark period) can be different.

The term "signal value" refers to a value of the sequencing signal output from a sequencing cell. According to certain embodiments, the sequencing signal is an electrical signal that is measured and/or output from a point in a circuit of one or more sequencing cells e.g., the signal value is (or represents) a voltage or a current. The signal value can represent the results of a direct measurement of voltage and/or current and/or may represent an indirect measurement, e.g., the signal value can be a measured duration of time for which it takes a voltage or current to reach a specified value. A signal value can represent any measurable quantity that correlates with the resistivity of a nanopore and from which the resistivity and/or conductance of the nanopore (threaded and/or unthreaded) can be derived. As another example, the signal value can correspond to a light intensity, e.g., from a fluorophore attached to a nucleotide being added to a nucleic acid with a polymerase.

The term "osmolarity", also known as osmotic concentration, refers to a measure of solute concentration. Osmolarity measures the number of osmoles of solute particles per unit volume of solution. An osmole is a measure of the number of moles of solute that contribute to the osmotic pressure of a solution. Osmolarity allows the measurement of the osmotic pressure of a solution and the determination of how the solvent will diffuse across a semipermeable membrane (osmosis) separating two solutions of different osmotic concentration.

The term "osmolyte" refers to any soluble compound that when dissolved into a solution increases the osmolarity of that solution.

DETAILED DESCRIPTION

According to certain embodiments, techniques and systems disclosed herein relate to insertion of a single pore into a membrane in a cell of a nanopore based sequencing chip. In some embodiments, the insertion of a pore into the membrane reduces the likelihood of insertion of an additional pore into the membrane, thereby self-limiting further pore insertion and reducing or eliminating the need for active feedback during the insertion step.

Example nanopore systems, circuitry, and sequencing operations are initially described, followed by example techniques to replace nanopores in DNA sequencing cells. Embodiments of the invention can be implemented in numerous ways, including as a process, a system, and a computer program product embodied on a computer readable storage medium and/or a processor, such as a processor configured to execute instructions stored on and/or provided by a memory coupled to the processor.

I. Nanopore Based Sequencing Chip

FIG. 1 is a top view of an embodiment of a nanopore sensor chip 100 having an array 140 of nanopore cells 150. Each nanopore cell 150 includes a control circuit integrated on a silicon substrate of nanopore sensor chip 100. In some embodiments, side walls 136 are included in array 140 to separate groups of nanopore cells 150 so that each group can receive a different sample for characterization. Each nanopore cell can be used to sequence a nucleic acid. In some embodiments, nanopore sensor chip 100 includes a cover plate 130. In some embodiments, nanopore sensor chip 100 also includes a plurality of pins 110 for interfacing with other circuits, such as a computer processor.

In some embodiments, nanopore sensor chip 100 includes multiple chips in a same package, such as, for example, a Multi-Chip Module (MCM) or System-in-Package (SiP). The chips can include, for example, a memory, a processor, a field-programmable gate array (FPGA), an application-specific integrated circuit (ASIC), data converters, a high-speed I/O interface, etc.

In some embodiments, nanopore sensor chip 100 is coupled to (e.g., docked to) a nanochip workstation 120, which can include various components for carrying out (e.g., automatically carrying out) various embodiments of the processes disclosed herein. These process can include, for example, analyte delivery mechanisms, such as pipettes for delivering lipid suspension or other membrane structure suspension, analyte solution, and/or other liquids, suspension or solids. The nanochip workstation components can further include robotic arms, one or more computer processors, and/or memory. A plurality of polynucleotides can be detected on array 140 of nanopore cells 150. In some embodiments, each nanopore cell 150 is individually addressable.

II. Nanopore Sequencing Cell

Nanopore cells 150 in nanopore sensor chip 100 can be implemented in many different ways. For example, in some embodiments, tags of different sizes and/or chemical structures are attached to different nucleotides in a nucleic acid molecule to be sequenced. In some embodiments, a complementary strand to a template of the nucleic acid molecule to be sequenced may be synthesized by hybridizing differently polymer-tagged nucleotides with the template. In some implementations, the nucleic acid molecule and the attached tags both move through the nanopore, and an ion current passing through the nanopore can indicate the nucleotide that is in the nanopore because of the particular size and/or structure of the tag attached to the nucleotide. In some implementations, only the tags are moved into the nanopore. There can also be many different ways to detect the different tags in the nanopores.

A. Nanopore Sequencing Cell Structure

Figure 2:
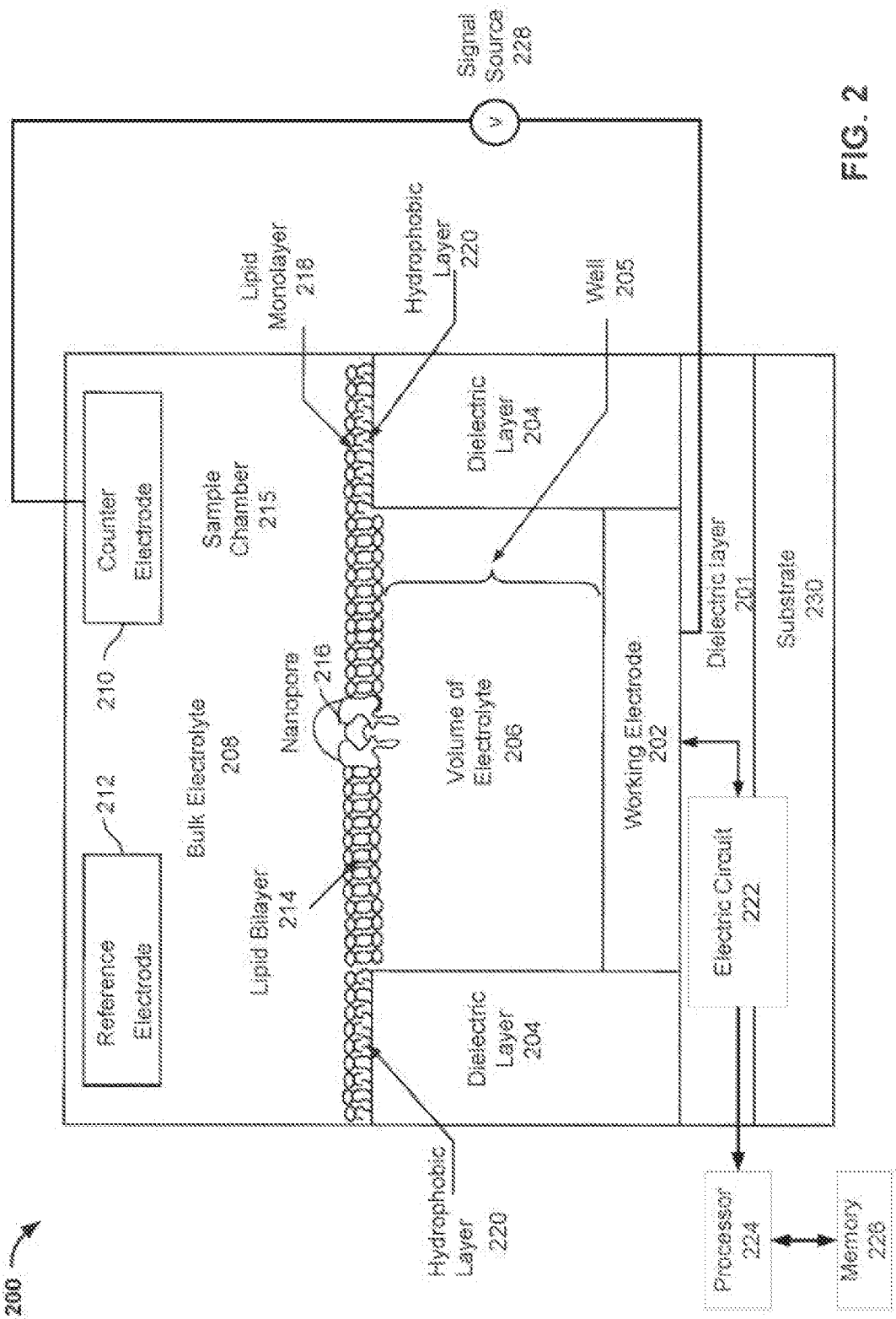
FIG. 2 illustrates an embodiment of a nanopore cell in a nanopore sensor chip that can be used to characterize a polynucleotide or a polypeptide.

FIG. 2 illustrates an embodiment of an example nanopore cell 200 in a nanopore sensor chip, such as nanopore cell 150 in nanopore sensor chip 100 of FIG. 1, that can be used to characterize a polynucleotide or a polypeptide. Nanopore cell 200 can include a well 205 formed of dielectric layers 201 and 204; a membrane, such as a lipid bilayer 214 formed over well 205; and a sample chamber 215 on lipid bilayer 214 and separated from well 205 by lipid bilayer 214. Well 205 can contain a volume of electrolyte 206, and sample chamber 215 can hold bulk electrolyte 208 containing a nanopore, e.g., a soluble protein nanopore transmembrane molecular complexes (PNTMC), and the analyte of interest (e.g., a nucleic acid molecule to be sequenced).

Nanopore cell 200 can include a working electrode 202 at the bottom of well 205 and a counter electrode 210 disposed in sample chamber 215. A signal source 228 can apply a voltage signal between working electrode 202 and counter electrode 210. A single nanopore (e.g., a PNTMC) can be inserted into lipid bilayer 214 by an electroporation process caused by the voltage signal, thereby forming a nanopore 216 in lipid bilayer 214. The individual membranes (e.g., lipid bilayers 214 or other membrane structures) in the array can be neither chemically nor electrically connected to each other. Thus, each nanopore cell in the array can be an independent sequencing machine, producing data unique to the single polymer molecule associated with the nanopore that operates on the analyte of interest and modulates the ionic current through the otherwise impermeable lipid bilayer.

Additional embodiments of systems and methods for pore insertion are described below in section III. In particular, these systems and methods describe self-limiting pore insertion that efficiently achieves single pore insertion in the membrane of the cell.

As shown in FIG. 2, nanopore cell 200 can be formed on a substrate 230, such as a silicon substrate. Dielectric layer 201 can be formed on substrate 230. Dielectric material used to form dielectric layer 201 can include, for example, glass, oxides, nitrides, and the like. An electric circuit 222 for controlling electrical stimulation and for processing the signal detected from nanopore cell 200 can be formed on substrate 230 and/or within dielectric layer 201. For example, a plurality of patterned metal layers (e.g., metal 1 to metal 6) can be formed in dielectric layer 201, and a plurality of active devices (e.g., transistors) can be fabricated on substrate 230. In some embodiments, signal source 228 is included as a part of electric circuit 222. Electric circuit 222 can include, for example, amplifiers, integrators, analog-to-digital converters, noise filters, feedback control logic, and/or various other components. Electric circuit 222 can be further coupled to a processor 224 that is coupled to a memory 226, where processor 224 can analyze the sequencing data to determine sequences of the polymer molecules that have been sequenced in the array.

Working electrode 202 can be formed on dielectric layer 201, and can form at least a part of the bottom of well 205. In some embodiments, working electrode 202 is a metal electrode. For non-faradaic conduction, working electrode 202 can be made of metals or other materials that are resistant to corrosion and oxidation, such as, for example, platinum, gold, titanium nitride, and graphite. For example, working electrode 202 can be a platinum electrode with electroplated platinum. In another example, working electrode 202 can be a titanium nitride (TiN) working electrode. Working electrode 202 can be porous, thereby increasing its surface area and a resulting capacitance associated with working electrode 202. Because the working electrode of a nanopore cell can be independent from the working electrode of another nanopore cell, the working electrode can be referred to as cell electrode in this disclosure.

Dielectric layer 204 can be formed above dielectric layer 201. Dielectric layer 204 forms the walls surrounding well 205. Dielectric material used to form dielectric layer 204 can include, for example, glass, oxide, silicon mononitride (SiN), polyimide, or other suitable hydrophobic insulating material. The top surface of dielectric layer 204 can be silanized. The silanization can form a hydrophobic layer 220 above the top surface of dielectric layer 204. In some embodiments, hydrophobic layer 220 has a thickness of about 1.5 nanometer (nm).

Well 205 formed by the dielectric layer walls 204 includes volume of electrolyte 206 above working electrode 202. Volume of electrolyte 206 can be buffered and can include one or more of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), manganese chloride ($MnCl_2$), and magnesium chloride ($MgCl_2$). In some embodiments, volume of electrolyte 206 has a thickness of about three microns ($\mu m$).

As also shown in FIG. 2, a membrane can be formed on top of dielectric layer 204 and spanning across well 205. In some embodiments, the membrane includes a lipid monolayer 218 formed on top of hydrophobic layer 220. As the membrane reaches the opening of well 205, lipid monolayer 208 can transition to lipid bilayer 214 that spans across the opening of well 205. The lipid bilayer can comprise or consist of lipids, such as a phospholipid, for example, selected from diphytanoyl-phosphatidylcholine (DPhPC), 1,2-diphytanoyl-sn-glycero-3-phosphocholine, 1,2-di-O-phytanyl-sn-glycero-3-phosphocholine (DoPhPC), palmitoyl-oleoyl-phosphatidylcholine (POPC), dioleoyl-phosphatidyl-methylester (DOPME), dipalmitoylphosphatidylcholine (DPPC), phosphatidylcholine, phosphatidylethanolamine, phosphatidylserine, phosphatidic acid, phosphatidylinositol, phosphatidylglycerol, sphingomyelin, 1,2-di-O-phytanyl-sn-glycerol, 1,2-dipalmitoyl-sn-glycero-3-phosphoethanolamine-N-[methoxy(polyethylene glycol)-350], 1,2-dipalmitoyl-sn-glycero-3-phosphoethanolamine-N-[methoxy(polyethylene glycol)-550], 1,2-dipalmitoyl-sn-glycero-3-phosphoethanolamine-N-[methoxy(polyethylene glycol)-750], 1,2-dipalmitoyl-sn-glycero-3-phosphoethanolamine-N-[methoxy(polyethylene glycol)-1000], 1,2-dipalmitoyl-sn-glycero-3-phosphoethanolamine-N-[methoxy(polyethylene glycol)-2000], 1,2-dioleoyl-sn-glycero-3-phosphoethanolamine-N-lactosyl, GM1 Ganglioside, Lysophosphatidylcholine (LPC), or any combination thereof. Other phospholipid derivatives may also be used, such as phosphatidic acid derivatives (e.g., DMPA, DDPA, DSPA), phosphatidylcholine derivatives (e.g., DDPC, DLPC, DMPC, DPPC, DSPC, DOPC, POPC, DEPC), phosphatidylglycerol derivatives (e.g., DMPG, DPPG, DSPG, POPG), phosphatidylethanolamine derivatives (e.g., DMPE, DPPE, DSPE DOPE), phosphatidylserine derivatives (e.g., DOPS), PEG phospholipid derivatives (e.g, mPEG-phospholipid, polyglycerin-phospholipid, functionalized-phospholipid, terminal activated-phospholipid), diphytanoyl phospholipids (e.g., DPhPC, DOPhPC, DPhPE, and DOPhPE), for example. In some embodiments, the bilayer can be formed using non-lipid based materials, such as amphiphilic block copolymers (e.g, poly(butadiene)-block-poly(ethylene oxide), PEG diblock copolymers, PEG triblock copolymers, PPG triblock copolymers, and poloxamers) and other amphiphilic copolymers, which may be nonionic or ionic. In some embodiments, the bilayer can be formed from a combination of lipid based materials and non-lipid based materials. In some embodiments, the bilayer materials can be delivered in a solvent phase including one or more organic solvents such as alkanes (e.g., decane, tridecane, hexadecane, etc.), and/or one or more silicone oils (e.g., AR-20).

As shown, lipid bilayer 214 is embedded with a single nanopore 216, e.g., formed by a single PNTMC. As described above, nanopore 216 can be formed by inserting a single PNTMC into lipid bilayer 214 by electroporation. Nanopore 216 can be large enough for passing at least a portion of the analyte of interest and/or small ions (e.g., $Na^+$, $K^+$, $Ca^{2+}$, $Cl^-$) between the two sides of lipid bilayer 214.

Sample chamber 215 is over lipid bilayer 214, and can hold a solution of the analyte of interest for characterization. The solution can be an aqueous solution containing bulk electrolyte 208 and buffered to an optimum ion concentration and maintained at an optimum pH to keep the nanopore 216 open. Nanopore 216 crosses lipid bilayer 214 and provides the only path for ionic flow from bulk electrolyte 208 to working electrode 202. In addition to nanopores (e.g., PNTMCs) and the analyte of interest, bulk electrolyte 208 can further include one or more of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), manganese chloride ($MnCl_2$), and magnesium chloride ($MgCl_2$).

Counter electrode (CE) 210 can be an electrochemical potential sensor. In some embodiments, counter electrode 210 is shared between a plurality of nanopore cells, and can therefore be referred to as a common electrode. In some cases, the common potential and the common electrode can be common to all nanopore cells, or at least all nanopore cells within a particular grouping. The common electrode can be configured to apply a common potential to the bulk electrolyte 208 in contact with the nanopore 216. Counter electrode 210 and working electrode 202 can be coupled to signal source 228 for providing electrical stimulus (e.g., voltage bias) across lipid bilayer 214, and can be used for sensing electrical characteristics of lipid bilayer 214 (e.g., resistance, capacitance, and ionic current flow). In some embodiments, nanopore cell 200 can also include a reference electrode 212.

In some embodiments, various checks are made during creation of the nanopore cell as part of calibration. Once a nanopore cell is created, further calibration steps can be performed, e.g., to identify nanopore cells that are performing as desired (e.g., one nanopore in the cell). Such calibration checks can include physical checks, voltage calibration, open channel calibration, and identification of cells with a single nanopore.

B. Detection Signals of Nanopore Sequencing Cell

Nanopore cells in nanopore sensor chip, such as nanopore cells 150 in nanopore sensor chip 100, can enable parallel sequencing using a single molecule nanopore based sequencing by synthesis (Nano-SBS) technique.

Figure 3:
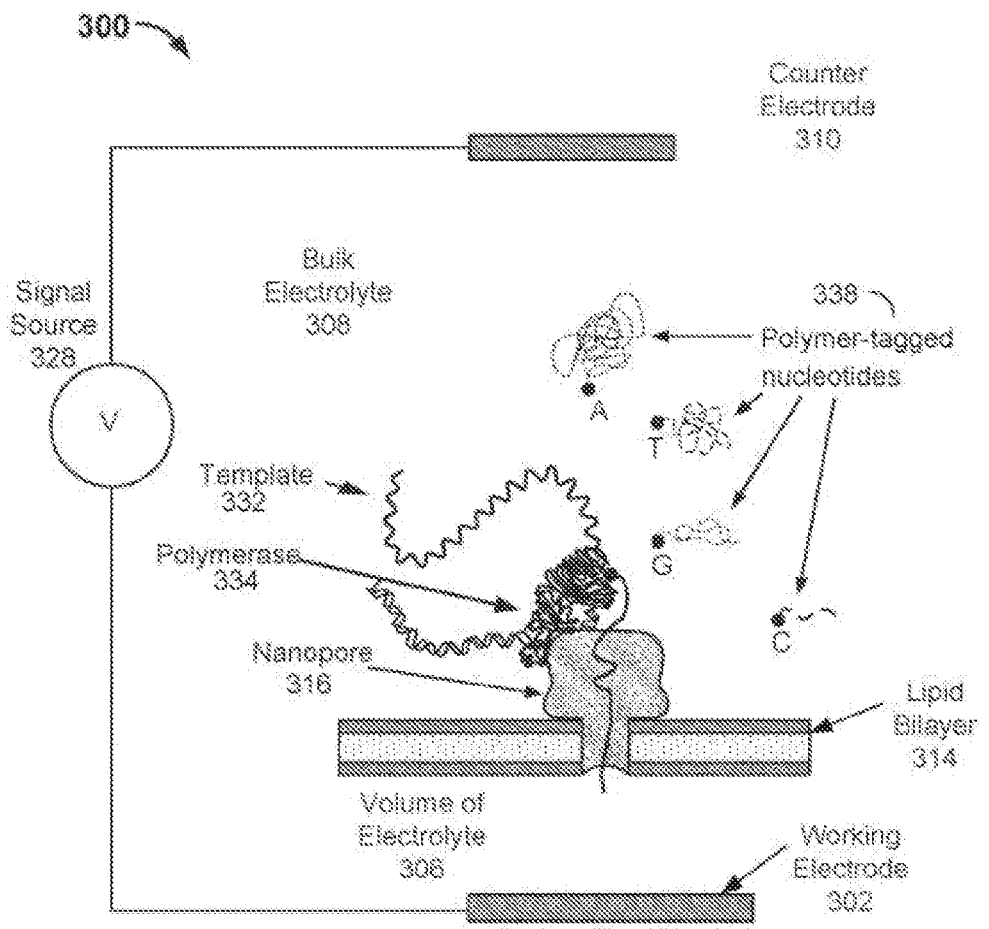
FIG. 3 illustrates an embodiment of a nanopore cell performing nucleotide sequencing using a nanopore based sequencing-by-synthesis (Nano-SBS) technique.
Figure 3:
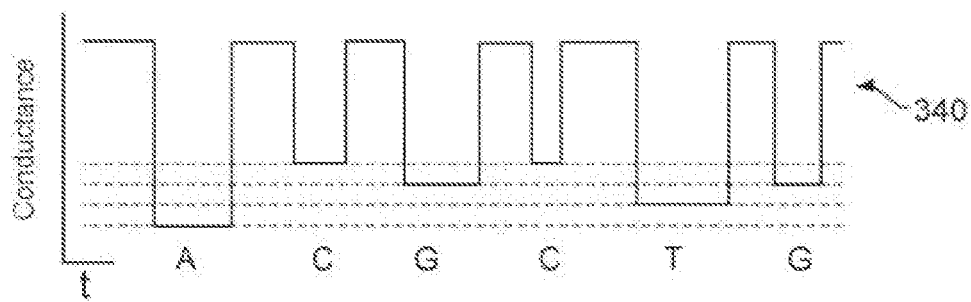

FIG. 3 illustrates an embodiment of a nanopore cell 300 performing nucleotide sequencing using the Nano-SBS technique. In the Nano-SBS technique, a template 332 to be sequenced (e.g., a nucleotide acid molecule or another analyte of interest) and a primer can be introduced into bulk electrolyte 308 in the sample chamber of nanopore cell 300. As examples, template 332 can be circular or linear. A nucleic acid primer can be hybridized to a portion of template 332 to which four differently polymer-tagged nucleotides 338 can be added.

In some embodiments, an enzyme (e.g., a polymerase 334, such as a DNA polymerase) is associated with nanopore 316 for use in the synthesizing a complementary strand to template 332. For example, polymerase 334 can be covalently attached to nanopore 316. Polymerase 334 can catalyze the incorporation of nucleotides 338 onto the primer using a single stranded nucleic acid molecule as the template. Nucleotides 338 can comprise tag species ("tags") with the nucleotide being one of four different types: A, T, G, or C. When a tagged nucleotide is correctly complexed with polymerase 334, the tag can be pulled (e.g., loaded) into the nanopore by an electrical force, such as a force generated in the presence of an electric field generated by a voltage applied across lipid bilayer 314 and/or nanopore 316 via a signal source 328 that is coupled to a working electrode 302 and counter electrode 310. The tail of the tag can be positioned in the barrel of nanopore 316. The tag held in the barrel of nanopore 316 can generate a unique ionic blockade signal 340 due to the tag's distinct chemical structure and/or size, thereby electronically identifying the added base to which the tag attaches.

As used herein, a "loaded" or "threaded" tag is one that is positioned in and/or remains in or near the nanopore for an appreciable amount of time, e.g., 0.1 millisecond (ms) to 10000 ms. In some cases, a tag is loaded in the nanopore prior to being released from the nucleotide. In some instances, the probability of a loaded tag passing through (and/or being detected by) the nanopore after being released upon a nucleotide incorporation event is suitably high, e.g., 90% to 99%.

In some embodiments, before polymerase 334 is connected to nanopore 316, the conductance of nanopore 316 is high, such as, for example, about 300 picosiemens (300 pS). As the tag is loaded in the nanopore, a unique conductance signal (e.g., signal 340) is generated due to the tag's distinct chemical structure and/or size. For example, the conductance of the nanopore can be about 60 pS, 80 pS, 100 pS, or 120 pS, each corresponding to one of the four types of tagged nucleotides. The polymerase can then undergo an isomerization and a transphosphorylation reaction to incorporate the nucleotide into the growing nucleic acid molecule and release the tag molecule.

In some cases, some of the tagged nucleotides may not match (complementary bases) with a current position of the nucleic acid molecule (template). The tagged nucleotides that are not base-paired with the nucleic acid molecule can also pass through the nanopore. These non-paired nucleotides can be rejected by the polymerase within a time scale that is shorter than the time scale for which correctly paired nucleotides remain associated with the polymerase. Tags bound to non-paired nucleotides can pass through the nanopore quickly, and be detected for a short period of time (e.g., less than 10 ms), while tags bounded to paired nucleotides can be loaded into the nanopore and detected for a long period of time (e.g., at least 10 ms). Therefore, non-paired nucleotides can be identified by a downstream processor based at least in part on the time for which the nucleotide is detected in the nanopore.

A conductance (or equivalently the resistance) of the nanopore including the loaded (threaded) tag can be measured via a signal value (e.g., voltage or a current passing through the nanopore), thereby providing an identification of the tag species and thus the nucleotide at the current position. In some embodiments, a direct current (DC) signal is applied to the nanopore cell (e.g., so that the direction in which the tag moves through the nanopore is not reversed). However, operating a nanopore sensor for long periods of time using a direct current can change the composition of the electrode, unbalance the ion concentrations across the nanopore, and have other undesirable effects that can affect the lifetime of the nanopore cell. Applying an alternating current (AC) waveform can reduce the electro-migration to avoid these undesirable effects and have certain advantages as described below. The nucleic acid sequencing methods described herein that utilize tagged nucleotides are fully compatible with applied AC voltages, and therefore an AC waveform can be used to achieve these advantages.

The ability to re-charge the electrode during the AC detection cycle can be advantageous when sacrificial electrodes, electrodes that change molecular character in the current-carrying reactions (e.g., electrodes comprising silver), or electrodes that change molecular character in current-carrying reactions are used. An electrode can deplete during a detection cycle when a direct current signal is used. The recharging can prevent the electrode from reaching a depletion limit, such as becoming fully depleted, which can be a problem when the electrodes are small (e.g., when the electrodes are small enough to provide an array of electrodes having at least 500 electrodes per square millimeter). Electrode lifetime in some cases scales with, and is at least partly dependent on, the width of the electrode.

Suitable conditions for measuring ionic currents passing through the nanopores are known in the art and examples are provided herein. The measurement can be carried out with a voltage applied across the membrane and pore. In some embodiments, the voltage used ranges from −400 mV to +400 mV. The voltage used is preferably in a range having a lower limit selected from −400 mV, −300 mV, −200 mV, −150 mV, −100 mV, −50 mV, −20 mV, and 0 mV, and an upper limit independently selected from +10 mV, +20 mV, +50 mV, +100 mV, +150 mV, +200 mV, +300 mV, and +400 mV. The voltage used can be more preferably in the range from 100 mV to 240 mV and most preferably in the range from 160 mV to 240 mV. It is possible to increase discrimination between different nucleotides by a nanopore using an increased applied potential. Sequencing nucleic acids using AC waveforms and tagged nucleotides is described in US Patent Publication No. US 2014/0134616 entitled "Nucleic Acid Sequencing Using Tags," filed on Nov. 6, 2013, which is herein incorporated by reference in its entirety. In addition to the tagged nucleotides described in US 2014/0134616, sequencing can be performed using nucleotide analogs that lack a sugar or acyclic moiety, e.g., (S)-glycerol nucleoside triphosphates (gNTPs) of the five common nucleobases: adenine, cytosine, guanine, uracil, and thymine (Horhota et al., Organic Letters, 8:5345-5347 [2006]).

C. Electric Circuit of Nanopore Sequencing Cell

Figure 4:
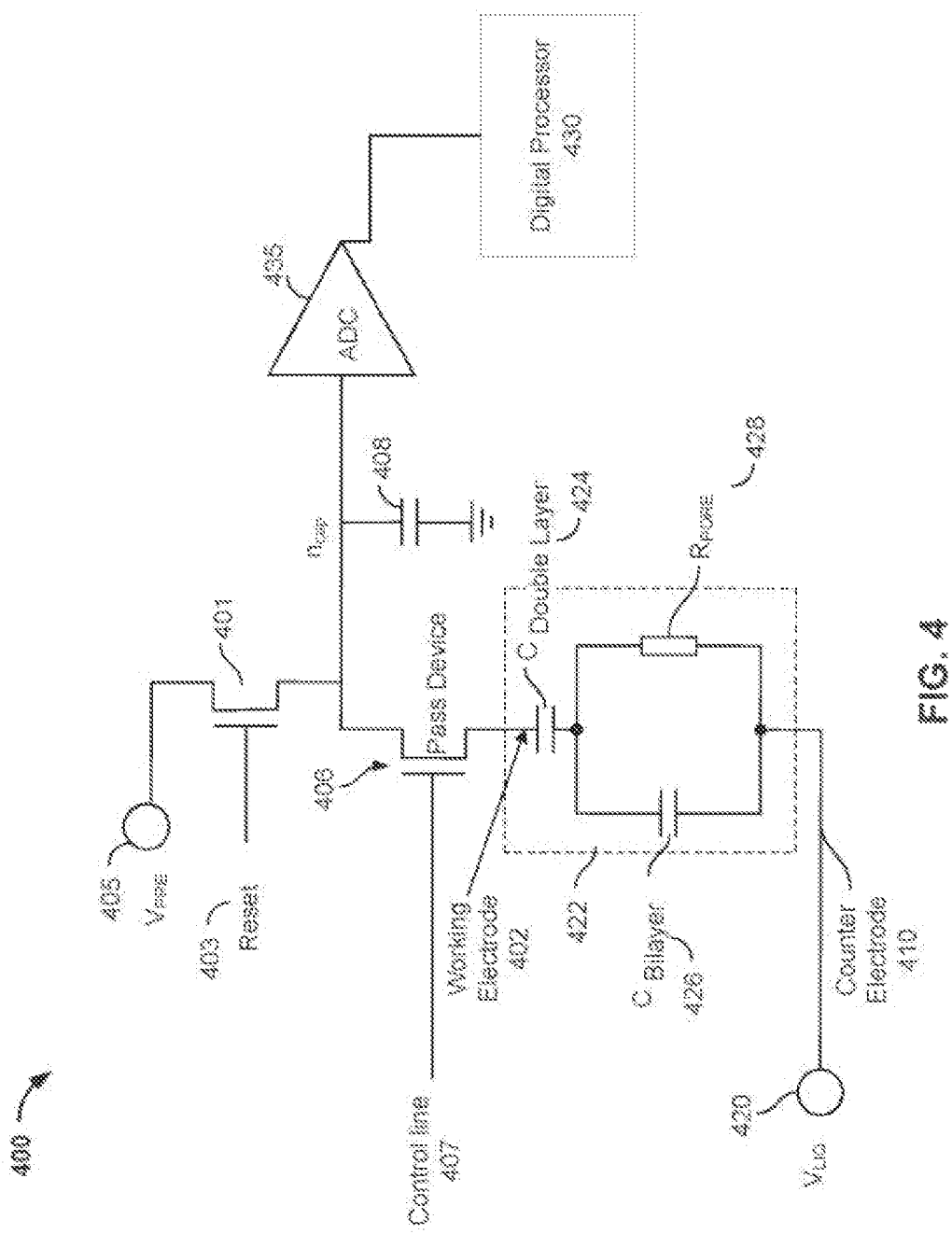
FIG. 4 illustrates an embodiment of an electric circuit in a nanopore cell.

FIG. 4 illustrates an embodiment of an electric circuit 400 (which may include portions of electric circuit 222 in FIG. 2) in a nanopore cell, such as nanopore cell 400. As described above, in some embodiments, electric circuit 400 includes a counter electrode 410 that can be shared between a plurality of nanopore cells or all nanopore cells in a nanopore sensor chip, and can therefore also be referred to as a common electrode. The common electrode can be configured to apply a common potential to the bulk electrolyte (e.g., bulk electrolyte 208) in contact with the lipid bilayer (e.g., lipid bilayer 214) in the nanopore cells by connecting to a voltage source $V_{LIQ}$ 420. In some embodiments, an AC non-Faradaic mode is utilized to modulate voltage $V_{LIQ}$ with an AC signal (e.g., a square wave) and apply it to the bulk electrolyte in contact with the lipid bilayer in the nanopore cell. In some embodiments, $V_{LIQ}$ is a square wave with a magnitude of ±200-250 mV and a frequency between, for example, 25 and 400 Hz. The bulk electrolyte between counter electrode 410 and the lipid bilayer (e.g., lipid bilayer 214) can be modeled by a large capacitor (not shown), such as, for example, 100 µF or larger.

FIG. 4 also shows an electrical model 422 representing the electrical properties of a working electrode 402 (e.g., working electrode 202) and the lipid bilayer (e.g., lipid bilayer 214). Electrical model 422 includes a capacitor 426 ($C_{Bilayer}$) that models a capacitance associated with the lipid bilayer and a resistor 428 ($R_{PORE}$) that models a variable resistance associated with the nanopore, which can change based on the presence of a particular tag in the nanopore. Electrical model 422 also includes a capacitor 424 having a double layer capacitance ($C_{Double\ Layer}$) and representing the electrical properties of working electrode 402 and well 205. Working electrode 402 can be configured to apply a distinct potential independent from the working electrodes in other nanopore cells.

Pass device 406 is a switch that can be used to connect or disconnect the lipid bilayer and the working electrode from electric circuit 400. Pass device 406 can be controlled by control line 407 to enable or disable a voltage stimulus to be applied across the lipid bilayer in the nanopore cell. Before lipids are deposited to form the lipid bilayer, the impedance between the two electrodes may be very low because the well of the nanopore cell is not sealed, and therefore pass device 406 can be kept open to avoid a short-circuit condition. Pass device 406 can be closed after lipid solvent has been deposited to the nanopore cell to seal the well of the nanopore cell.

Circuitry 400 can further include an on-chip integrating capacitor 408 ($n_{cap}$). Integrating capacitor 408 can be precharged by using a reset signal 403 to close switch 401, such that integrating capacitor 408 is connected to a voltage source $V_{PRE}$ 405. In some embodiments, voltage source $V_{PRE}$ 405 provides a constant reference voltage with a magnitude of, for example, 900 mV. When switch 401 is closed, integrating capacitor 408 can be pre-charged to the reference voltage level of voltage source $V_{PRE}$ 405.

After integrating capacitor 408 is pre-charged, reset signal 403 can be used to open switch 401 such that integrating capacitor 408 is disconnected from voltage source $V_{PRE}$ 405. At this point, depending on the level of voltage source $V_{LIQ}$, the potential of counter electrode 410 can be at a higher level than that of the potential of working electrode 402 (and integrating capacitor 408), or vice versa. For example, during a positive phase of a square wave from voltage source $V_{LIQ}$ (e.g., the bright or dark period of the AC voltage source signal cycle), the potential of counter electrode 410 is at a level higher than the potential of working electrode 402. During a negative phase of the square wave from voltage source $V_{LIQ}$ (e.g., the dark or bright period of the AC voltage source signal cycle), the potential of counter electrode 410 is at a lower level than that of the potential of working electrode 402. Thus, in some embodiments, integrating capacitor 408 can be further charged during the bright period from the pre-charged voltage level of voltage source $V_{PRE}$ 405 to a higher level, and discharged during the dark period to a lower level, due to the potential difference between counter electrode 410 and working electrode 402. In other embodiments, the charging and discharging occur in dark periods and bright periods, respectively.

Integrating capacitor 408 can be charged or discharged for a fixed period of time, depending on the sampling rate of an analog-to-digital converter (ADC) 435, which can be higher than 1 kHz, 5 kHz, 10 kHz, 100 kHz, or more. For example, with a sampling rate of 1 kHz, integrating capacitor 408 can be charged/discharged for a period of about 1 ms, and then the voltage level can be sampled and converted by ADC 435 at the end of the integration period. A particular voltage level would correspond to a particular tag species in the nanopore, and thus correspond to the nucleotide at a current position on the template.

After being sampled by ADC 435, integrating capacitor 408 can be pre-charged again by using reset signal 403 to close switch 401, such that integrating capacitor 408 is connected to voltage source $V_{PRE}$ 405 again. The steps of pre-charging integrating capacitor 408, waiting for a fixed period of time for integrating capacitor 408 to charge or discharge, and sampling and converting the voltage level of integrating capacitor by ADC 435 can be repeated in cycles throughout the sequencing process.

A digital processor 430 can process the ADC output data, e.g., for normalization, data buffering, data filtering, data compression, data reduction, event extraction, or assembling ADC output data from the array of nanopore cells into various data frames. In some embodiments, digital processor 430 performs further downstream processing, such as base determination. Digital processor 430 can be implemented as hardware (e.g., in a graphics processing unit (GPU), FPGA, ASIC, etc.) or as a combination of hardware and software.

Accordingly, the voltage signal applied across the nanopore can be used to detect particular states of the nanopore. One of the possible states of the nanopore is an open-channel state when a tag-attached polyphosphate is absent from the barrel of the nanopore, also referred to herein as the unthreaded state of the nanopore. Another four possible states of the nanopore each correspond to a state when one of the four different types of tag-attached polyphosphate nucleotides (A, T, G, or C) is held in the barrel of the nanopore. Yet another possible state of the nanopore is when the lipid bilayer is ruptured.

When the voltage level on integrating capacitor 408 is measured after a fixed period of time, the different states of a nanopore can result in measurements of different voltage levels. This is because the rate of the voltage decay (decrease by discharging or increase by charging) on integrating capacitor 408 (i.e., the steepness of the slope of a voltage on integrating capacitor 408 versus time plot) depends on the nanopore resistance (e.g., the resistance of resistor $R_{PORE}$ 428). More particularly, as the resistance associated with the nanopore in different states is different due to the molecules' (tags') distinct chemical structures, different corresponding rates of voltage decay can be observed and can be used to identify the different states of the nanopore. The voltage decay curve can be an exponential curve with an RC time constant $\tau=RC$, where R is the resistance associated with the nanopore (i.e., $R_{PORE}$ resistor 428) and C is the capacitance associated with the membrane (i.e., $C_{Bilayer}$ capacitor 426) in parallel with R. A time constant of the nanopore cell can be, for example, about 200-500 ms. The decay curve may not fit exactly to an exponential curve due to the detailed implementation of the bilayer, but the decay curve can be similar to an exponential curve and be monotonic, thus allowing detection of tags.

In some embodiments, the resistance associated with the nanopore in an open-channel state is in the range of 100 MOhm to 20 GOhm. In some embodiments, the resistance associated with the nanopore in a state where a tag is inside the barrel of the nanopore can be within the range of 200 MOhm to 40 GOhm. In other embodiments, integrating capacitor 408 is omitted, as the voltage leading to ADC 435 will still vary due to the voltage decay in electrical model 422.

The rate of the decay of the voltage on integrating capacitor 408 can be determined in different ways. As explained above, the rate of the voltage decay can be determined by measuring a voltage decay during a fixed time interval. For example, the voltage on integrating capacitor 408 can be first measured by ADC 435 at time t1, and then the voltage is measured again by ADC 435 at time t2. The voltage difference is greater when the slope of the voltage on integrating capacitor 408 versus time curve is steeper, and the voltage difference is smaller when the slope of the voltage curve is less steep. Thus, the voltage difference can be used as a metric for determining the rate of the decay of the voltage on integrating capacitor 408, and thus the state of the nanopore cell.

In other embodiments, the rate of the voltage decay is determined by measuring a time duration that is required for a selected amount of voltage decay. For example, the time required for the voltage to drop or increase from a first voltage level V1 to a second voltage level V2 can be measured. The time required is less when the slope of the voltage vs. time curve is steeper, and the time required is greater when the slope of the voltage vs. time curve is less steep. Thus, the measured time required can be used as a metric for determining the rate of the decay of the voltage on integrating capacitor $n_{cap}$ 408, and thus the state of the nanopore cell. One skilled in the art will appreciate the various circuits that can be used to measure the resistance of the nanopore, e.g., including signal value measurement techniques, such as voltage or current measurements.

In some embodiments, electric circuit 400 does not include a pass device (e.g., pass device 406) and an extra capacitor (e.g., integrating capacitor 408 ($n_{cap}$)) that are fabricated on-chip, thereby facilitating the reduction in size of the nanopore based sequencing chip. Due to the thin nature of the membrane (lipid bilayer), the capacitance associated with the membrane (e.g., capacitor 426 ($C_{Bilayer}$)) alone can suffice to create the required RC time constant without the need for additional on-chip capacitance. Therefore, capacitor 426 can be used as the integrating capacitor, and can be pre-charged by the voltage signal $V_{PRE}$ and subsequently be discharged or charged by the voltage signal $V_{LIQ}$. The elimination of the extra capacitor and the pass device that are otherwise fabricated on-chip in the electric circuit can significantly reduce the footprint of a single nanopore cell in the nanopore sequencing chip, thereby facilitating the scaling of the nanopore sequencing chip to include more and more cells (e.g., having millions of cells in a nanopore sequencing chip).

D. Data Sampling in Nanopore Cell

To perform sequencing of a nucleic acid, the voltage level of integrating capacitor (e.g., integrating capacitor 408 ($n_{cap}$) or capacitor 426 ($C_{Bilayer}$)) can be sampled and converted by the ADC (e.g., ADC 435) while a tagged nucleotide is being added to the nucleic acid. The tag of the nucleotide can be pushed into the barrel of the nanopore by the electric field across the nanopore that is applied through the counter electrode and the working electrode, for example, when the applied voltage is such that $V_{LIQ}$ is lower than $V_{PRE}$.

1. Threading

A threading event is when a tagged nucleotide is attached to the template (e.g., nucleic acid fragment), and the tag moves in and out of the barrel of the nanopore. This movement can happen multiple times during a threading event. When the tag is in the barrel of the nanopore, the resistance of the nanopore can be higher, and a lower current can flow through the nanopore.

During sequencing, a tag may not be in the nanopore in some AC cycles (referred to as an open-channel state), where the current is the highest because of the lower resistance of the nanopore. When a tag is attracted into the barrel of the nanopore, the nanopore is in a bright mode. When the tag is pushed out of the barrel of the nanopore, the nanopore is in a dark mode.

2. Bright and Dark Period

During an AC cycle, the voltage on integrating capacitor can be sampled multiple times by the ADC. For example, in one embodiment, an AC voltage signal is applied across the system at, e.g., about 100 Hz, and an acquisition rate of the ADC can be about 2000 Hz per cell. Thus, there can be about 20 data points (voltage measurements) captured per AC cycle (cycle of an AC waveform). Data points corresponding to one cycle of the AC waveform can be referred to as a set. In a set of data points for an AC cycle, there can be a subset captured when, for example, $V_{LIQ}$ is lower than $V_{PRE}$, which can correspond to a bright mode (period) when the tag is forced into the barrel of the nanopore. Another subset can correspond to a dark mode (period) when the tag is pushed out of the barrel of the nanopore by the applied electric field when, for example, $V_{LIQ}$ is higher than $V_{PRE}$.

3. Measured Voltages

For each data point, when the switch 401 is opened, the voltage at the integrating capacitor (e.g., integrating capacitor 408 ($n_{cap}$) or capacitor 426 ($C_{Bilayer}$)) will change in a decaying manner as a result of the charging/discharging by $V_{LIQ}$, e.g., as an increase from $V_{PRE}$ to $V_{LIQ}$ when $V_{LIQ}$ is higher than $V_{PRE}$ or a decrease from $V_{PRE}$ to $V_{LIQ}$ when $V_{LIQ}$ is lower than $V_{PRE}$. The final voltage values can deviate from $V_{LIQ}$ as the working electrode charges. The rate of change of the voltage level on the integrating capacitor can be governed by the value of the resistance of the bilayer, which can include the nanopore, which can in turn include a molecule (e.g., a tag of a tagged nucleotides) in the nanopore. The voltage level can be measured at a predetermined time after switch 401 opens.

Switch 401 can operate at the rate of data acquisition. Switch 401 can be closed for a relatively short time period between two acquisitions of data, typically right after a measurement by the ADC. The switch allows multiple data points to be collected during each sub-period (bright or dark) of each AC cycle of $V_{LIQ}$. If switch 401 remains open, the voltage level on the integrating capacitor, and thus the output value of the ADC, fully decays and stays there. If instead switch 401 is closed, the integrating capacitor is precharged again (to $V_{PRE}$) and becomes ready for another measurement. Thus, switch 401 allows multiple data points to be collected for each sub-period (bright or dark) of each AC cycle. Such multiple measurements can allow higher resolution with a fixed ADC (e.g. 8-bit to 14-bit due to the greater number of measurements, which may be averaged). The multiple measurements can also provide kinetic information about the molecule threaded into the nanopore. The timing information can allow the determination of how long a threading takes place. This can also be used in helping to determine whether multiple nucleotides that are added to the nucleic acid strand are being sequenced.

Figure 5:
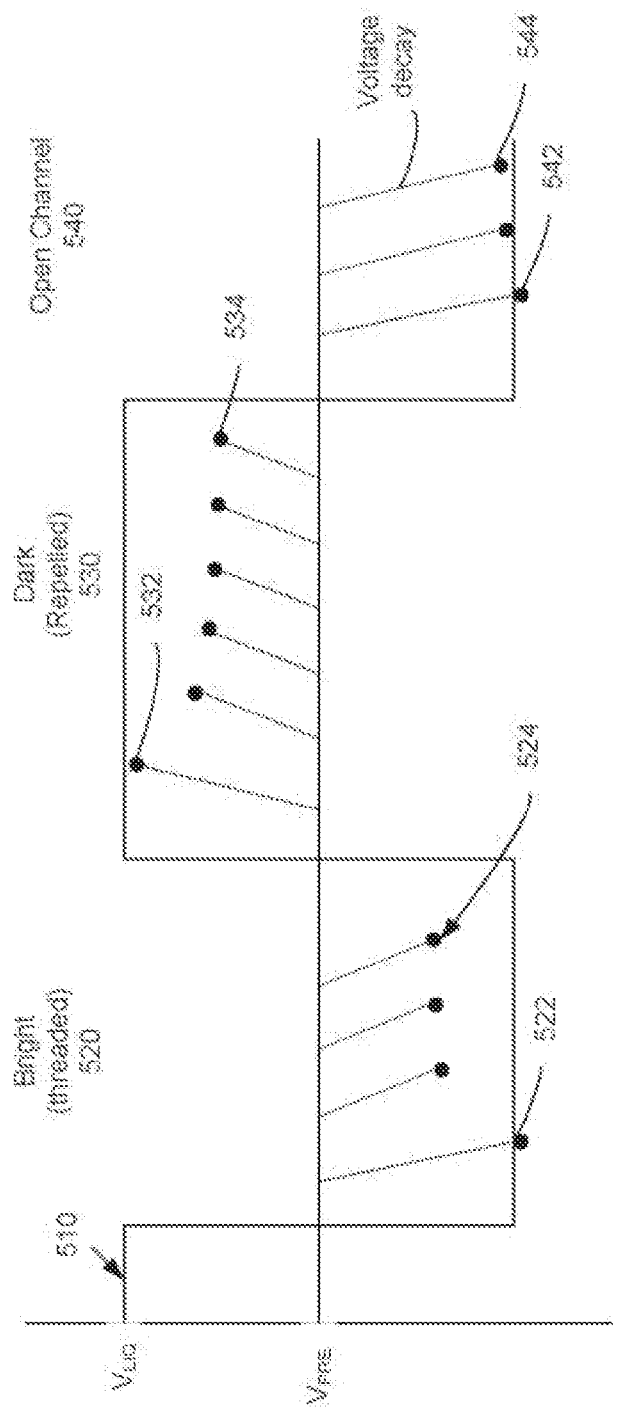
FIG. 5 shows example data points captured from a nanopore cell during bright periods and dark periods of AC cycles.

FIG. 5 shows example data points captured from a nanopore cell during bright periods and dark periods of AC cycles. In FIG. 5, the change in the data points is exaggerated for illustration purpose. The voltage ($V_{PRE}$) applied to the working electrode or the integrating capacitor is at a constant level, such as, for example, 900 mV. A voltage signal 510 ($V_{LIQ}$) applied to the counter electrode of the nanopore cells is an AC signal shown as a rectangular wave, where the duty cycle can be any suitable value, such as less than or equal to 50%, for example, about 40%.

During a bright period 520, voltage signal 510 ($V_{LIQ}$) applied to the counter electrode is lower than the voltage $V_{PRE}$ applied to the working electrode, such that a tag can be forced into the barrel of the nanopore by the electric field caused by the different voltage levels applied at the working electrode and the counter electrode (e.g., due to the charge on the tag and/or flow of the ions). When switch 401 is opened, the voltage at a node before the ADC (e.g., at an integrating capacitor) will decrease. After a voltage data point is captured (e.g., after a specified time period), switch 401 can be closed and the voltage at the measurement node will increase back to $V_{PRE}$ again. The process can repeat to measure multiple voltage data points. In this way, multiple data points can be captured during the bright period.

As shown in FIG. 5, a first data point 522 (also referred to as first point delta (FPD)) in the bright period after a change in the sign of the $V_{LIQ}$ signal can be lower than subsequent data points 524. This can be because there is no tag in the nanopore (open channel), and thus it has a low resistance and a high discharge rate. In some instances, first data point 522 can exceed the $V_{LIQ}$ level as shown in FIG. 5. This can be caused by the capacitance of the bilayer coupling the signal to the on-chip capacitor. Data points 524 can be captured after a threading event has occurred, i.e., a tag is forced into the barrel of the nanopore, where the resistance of the nanopore and thus the rate of discharging of the integrating capacitor depends on the particular type of tag that is forced into the barrel of the nanopore. Data points 524 can decrease slightly for each measurement due to charge built up at $C_{Double\ Layer}$ 424, as mentioned below.

During a dark period 530, voltage signal 510 ($V_{LIQ}$) applied to the counter electrode is higher than the voltage ($V_{PRE}$) applied to the working electrode, such that any tag would be pushed out of the barrel of the nanopore. When switch 401 is opened, the voltage at the measurement node increases because the voltage level of voltage signal 510 ($V_{LIQ}$) is higher than $V_{PRE}$. After a voltage data point is captured (e.g., after a specified time period), switch 401 can be closed and the voltage at the measurement node will decrease back to $V_{PRE}$ again. The process can repeat to measure multiple voltage data points. Thus, multiple data points can be captured during the dark period, including a first point delta 532 and subsequent data points 534. As described above, during the dark period, any nucleotide tag is pushed out of the nanopore, and thus minimal information about any nucleotide tag is obtained, besides for use in normalization.

FIG. 5 also shows that during bright period 540, even though voltage signal 510 ($V_{LIQ}$) applied to the counter electrode is lower than the voltage ($V_{PRE}$) applied to the working electrode, no threading event occurs (open-channel). Thus, the resistance of the nanopore is low, and the rate of discharging of the integrating capacitor is high. As a result, the captured data points, including a first data point 542 and subsequent data points 544, show low voltage levels.

The voltage measured during a bright or dark period might be expected to be about the same for each measurement of a constant resistance of the nanopore (e.g., made during a bright mode of a given AC cycle while one tag is in the nanopore), but this may not be the case when charge builds up at double layer capacitor 424 (C Double Layer). This charge build-up can cause the time constant of the nanopore cell to become longer. As a result, the voltage level may be shifted, thereby causing the measured value to decrease for each data point in a cycle. Thus, within a cycle, the data points may change somewhat from data point to another data point, as shown in FIG. 5.

Further details regarding measurements can be found in, for example, U.S. Patent Publication No. 2016/0178577 entitled "Nanopore-Based Sequencing With Varying Voltage Stimulus," U.S. Patent Publication No. 2016/0178554 entitled "Nanopore-Based Sequencing With Varying Voltage Stimulus," U.S. patent application Ser. No. 15/085,700 entitled "Non-Destructive Bilayer Monitoring Using Measurement Of Bilayer Response To Electrical Stimulus," and U.S. patent application Ser. No. 15/085,713 entitled "Electrical Enhancement Of Bilayer Formation," the disclosures of which are incorporated by reference in their entirety for all purposes.

4. Normalization and Base Calling

For each usable nanopore cell of the nanopore sensor chip, a production mode can be run to sequence nucleic acids. The ADC output data captured during the sequencing can be normalized to provide greater accuracy. Normalization can account for offset effects, such as cycle shape, gain drift, charge injection offset, and baseline shift. In some implementations, the signal values of a bright period cycle corresponding to a threading event can be flattened so that a single signal value is obtained for the cycle (e.g., an average) or adjustments can be made to the measured signal to reduce the intra-cycle decay (a type of cycle shape effect). Gain drift generally scales entire signal and changes on the order to 100s to 1,000s of seconds. As examples, gain drift can be triggered by changes in solution (pore resistance) or changes in bilayer capacitance. The baseline shift occurs with a timescale of ~100 ms, and relates to a voltage offset at the working electrode. The baseline shift can be driven by changes in an effective rectification ratio from threading as a result of a need to maintain charge balance in the sequencing cell from the bright period to the dark period.

After normalization, embodiments can determine clusters of voltages for the threaded channels, where each cluster corresponds to a different tag species, and thus a different nucleotide. The clusters can be used to determine probabilities of a given voltage corresponding to a given nucleotide. As another example, the clusters can be used to determine cutoff voltages for discriminating between different nucleotides (bases).

III. Self-Limiting Pore Insertion

After a pore is inserted into a membrane of a cell, the voltage across the membrane begins to drop rapidly due to the relatively high conductance of the pore. The decrease in voltage across the membrane reduces the driving force for additional pore insertion in the membrane.

Figure 6:
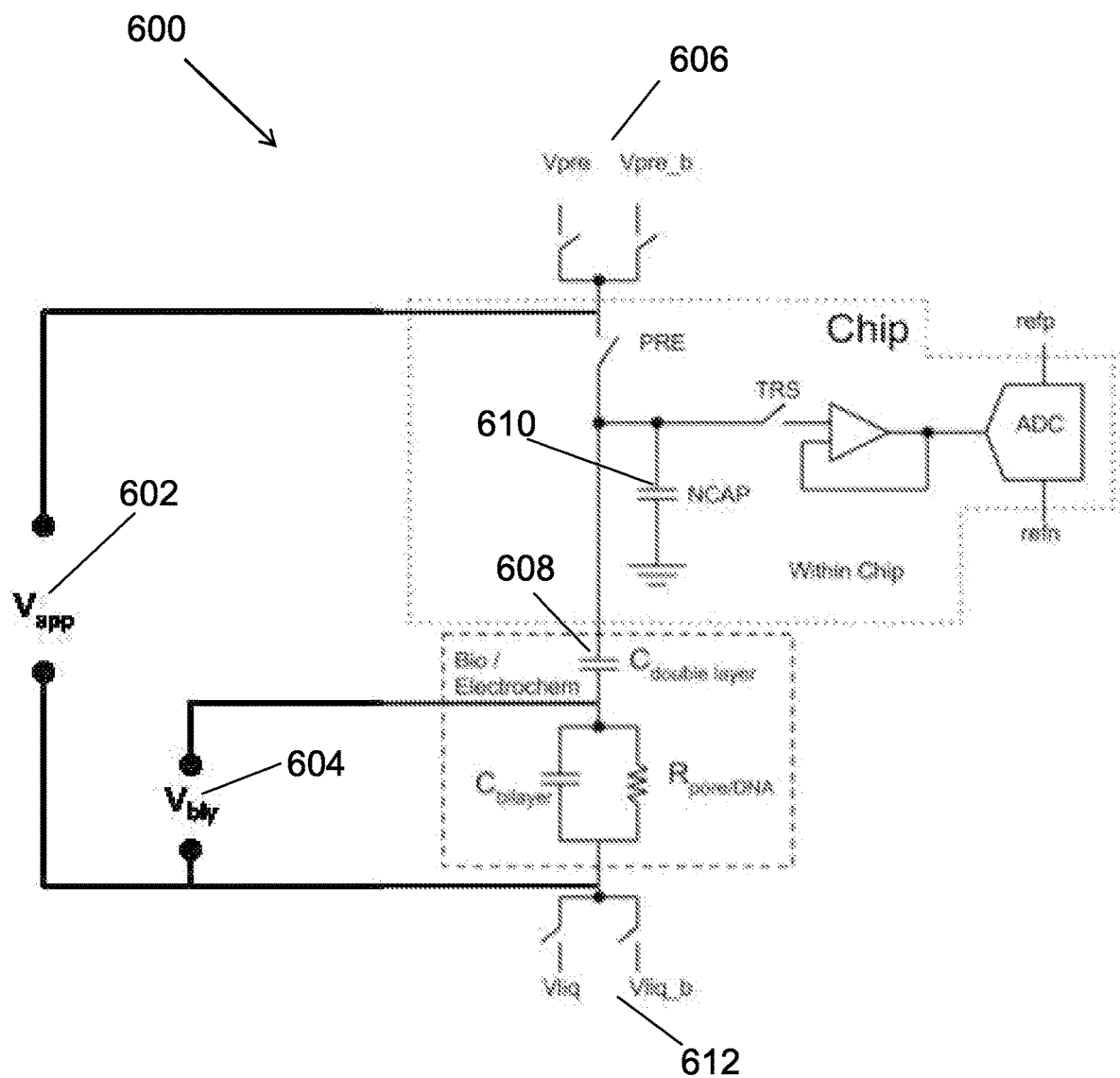
FIG. 6 illustrates an embodiment of a circuit diagram of a nanopore sensor cell.

FIG. 6 illustrates an embodiment of a circuit diagram 600 for a nanopore sensor cell that highlights some of the various voltages and components of the sensor cell that can be relevant to the systems and methods described herein, such as the voltage (Vapp) 602 that is applied between the working electrode and the counter electrode, the voltage (Vbly) 604 across the bilayer, the voltage (Vpre) 606 that is used to precharge the working electrode (Cdoublelayer) 608 and integrating capacitor (NCAP) 610, and the voltage (Vliq) 612 which is applied to the counter electrode.

Described herein are methods and systems that take advantage of this property to insert protein pores and control for single pore insertion without active feedback during the insertion step. In some embodiments of this pore insertion method, an AC coupled voltage is applied via capacitive working electrodes, and the voltage is maintained across the membrane by the low conductance of the poreless membrane. In some embodiments, the voltage can be applied to the entire array of cells, agnostic to the current state of pore insertion. In some embodiments, the voltage can be applied to cells having a membrane. The voltage waveform that is applied can be increased gradually as a ramp, as a plurality of increasing steps, or other shapes designed to yield low probability of additional protein pore insertion while also reducing the risk of membrane damage. This can be achieved by limiting the voltage application transients by using small voltage steps, modest rates of voltage increase in a voltage ramp, or the like.

Figure 7:
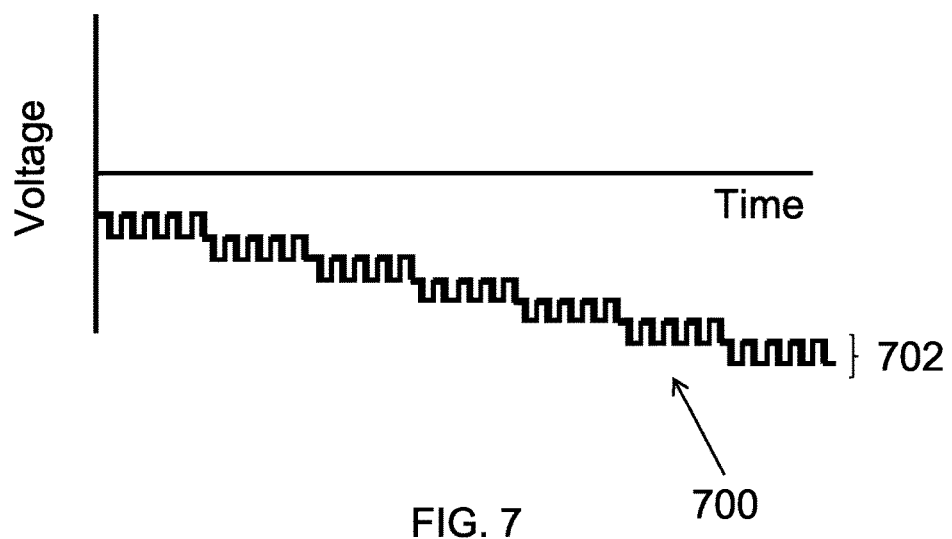
FIG. 7 illustrates a stepped voltage waveform that can be used to facilitate pore insertion.

For example, in some embodiments as shown in FIG. 7, the pore insertion voltage (Vapp) can be applied as a stepped voltage waveform 700 that starts at 0 mV and is increased in 100 mV increments every 5 seconds up to a maximum voltage of 600 mV. In some embodiments, the initial voltage can be about 0, 10, 20, 30, 40, 50, 60, 70, 80, 90, or 100 mV. In some embodiments, the step increase can be about 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 mV. In some embodiments, the duration of each step can be about 0.1, 0.2, 0.3, 0.4, 0.5, 0.6, 0.7, 0.8, 0.9, 1, 2, 3, 4, 5, 6, 7, 8, 9, 10, 20, 30, 40, 50, or 60 seconds. In some embodiments, the steps can have a variable duration. For example, in some embodiments, some or all the steps at the lower voltages can have a longer duration than steps at the higher voltages. In some embodiments, the maximum voltage is about 100, 200, 300, 400, 500, 600, 700, 800, 900, 1000, 1100, 1200, 1300, 1400, 1500, 1600, 1700, 1800, 1900, or 2000 mV. In some embodiments, one or more elements of the pore insertion voltage waveform can be predetermined, such as the initial starting voltage, the magnitude of the voltage step increase, the duration of each step, and/or the maximum voltage.

Figure 8A:
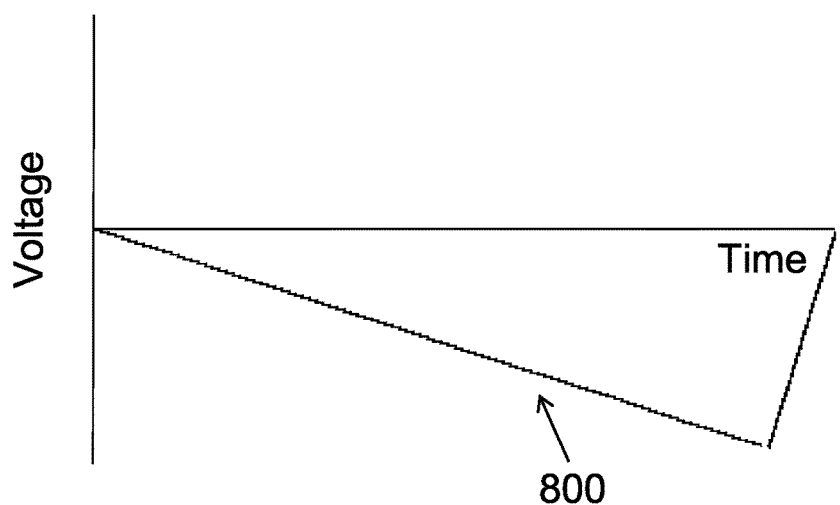
FIGS. 8A and 8B illustrate a ramp voltage waveform that can be used to facilitate pore insertion.

In some embodiments as shown in FIG. 8A, the pore insertion voltage can be applied as a ramped voltage waveform 800 that starts at 0 mV and is increased at a rate of 1 V per minute up to a maximum voltage of 600 mV. In some embodiments, the initial voltage can be about 0, 10, 20, 30, 40, 50, 60, 70, 80, 90, or 100 mV. In some embodiments, the rate of voltage increase is about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0 V per minute. In some embodiments, the maximum voltage is about 100, 200, 300, 400, 500, 600, 700, 800, 900, 1000, 1100, 1200, 1300, 1400, 1500, 1600, 1700, 1800, 1900, or 2000 mV. In some embodiments, one or more elements of the pore insertion voltage waveform can be predetermined, such as the initial starting voltage, the rate of voltage increase, and/or the maximum voltage.

In some embodiments, one or more elements of the pore insertion voltage waveform can be determined based on measured electrical and/or physical properties of components of the cell, such as membrane seal resistance, which is the resistance across the membrane after it forms a seal across a cell. In some embodiments, these measurements can be taken before the voltage waveform is applied such that the waveform is completely determined before being applied, in contrast to an active feedback based method which uses measurements taken during stimulation to alter one or more stimulation parameters. Because the methods of poration described herein are self-limiting, there is no need to utilize active poration methods that involve measuring a change in an electrical or physical property of the system or component of the system that results from a pore inserting into the membrane, and then adjusting the poration voltage in response in order to prevent insertion of a second pore into the membrane.

In some embodiments, the methods described herein can be applied to an array of sensors with capacitive electrodes at the base of microwells with suspended membranes and a counter electrode on the other side of the membrane. The sensors can be used to detect the presence of a pore after the insertion driving voltage application is removed from all cells. Although it is possible to detect the presence of a pore during the voltage application, it is not necessary in this method, and pores can be inserted with no feedback to voltage application on any individual sensor in the array or in aggregate.

The method effectively scans through the voltages required to overcome the pore insertion activation barrier, which may vary between individual membranes in the array, between small or large regions on the array, or between an array from one device to another array from a second device. In addition, the poration voltage may vary between pore mutants, between membrane compositions and conformations including lipid bilayers, block copolymers, or other implementations. By scanning or sweeping the voltages across a low to high range, a single voltage waveform can be robust enough to effectively work on a large number of different types of pore arrays or pore arrays of the same type with a certain amount of variability.

Figure 9A:
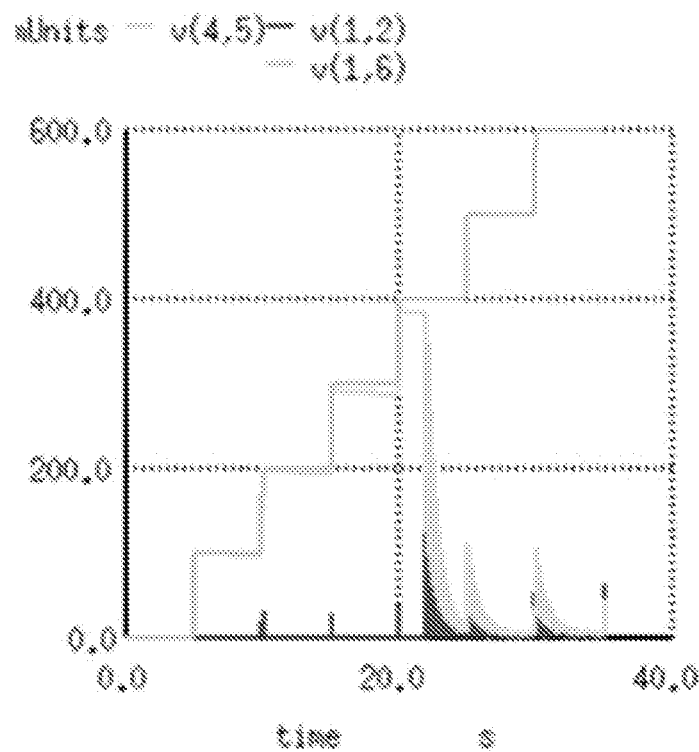
FIGS. 9A and 9B illustrate that in some embodiments, once the pore has been inserted, the pore can dissipate voltage buildup across the membrane itself, thereby both reducing the risk of damage to the membrane when the voltage is further increased after the pore has been inserted and reducing the likelihood of additional pore insertion.
Figure 9B:
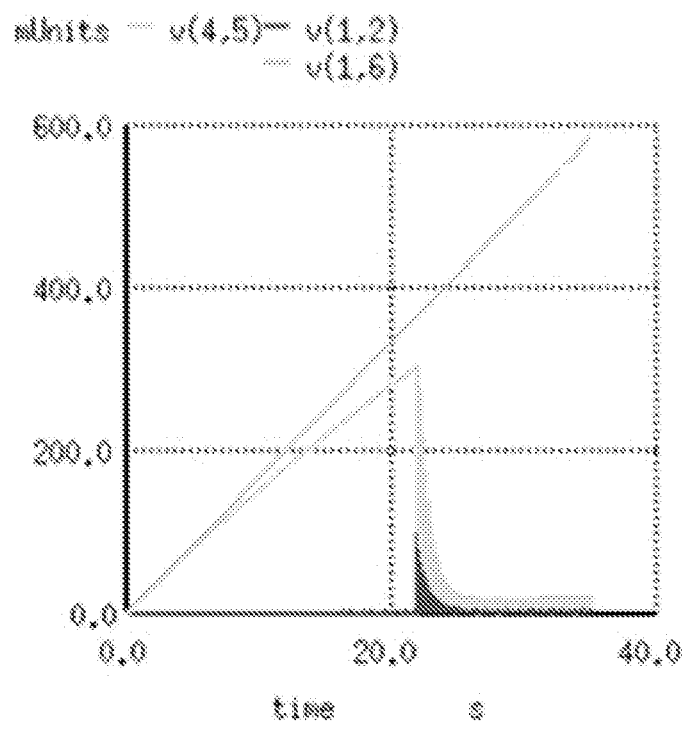

In addition, by sweeping from a low to high voltage, pores can be more likely inserted in the membrane before the bilayer reaches a critical voltage level that damages the membrane. In addition, as shown in FIGS. 9A and 9B, once the pore has been inserted, the pore can dissipate voltage buildup across the membrane, thereby both reducing the risk of damage to the membrane when the voltage is further increased after the pore has been inserted and reducing the likelihood of additional pore insertion. As long as the magnitude of the voltage steps or rate of increase of the voltage ramp is not too great, the pore can effectively dissipate excessive voltage buildup across the membrane, thereby reducing the risk of damaging the membrane and reducing the likelihood of additional pore insertion. On the other hand, it would be desirable to increase the magnitude of the voltage steps or increase the rate of increase of the voltage ramp in order to reduce the time it takes to complete the poration step.

Figure 10A:
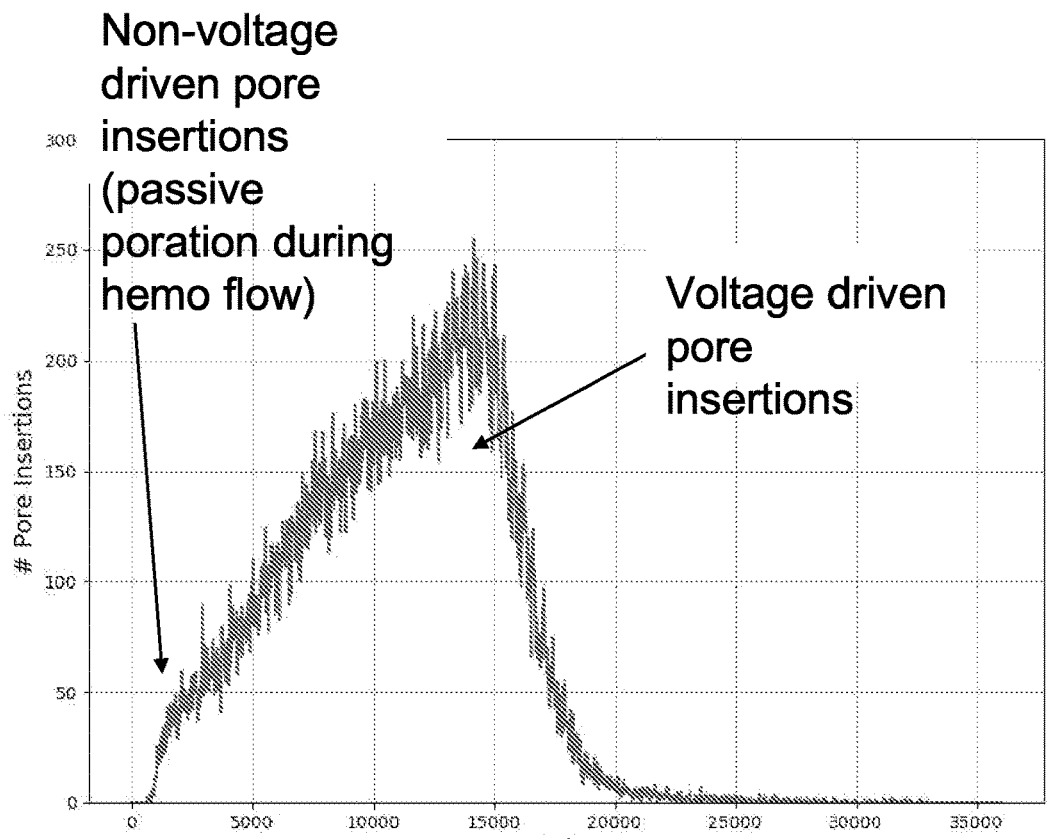
FIG. 10A illustrates a plot of the number of pore insertions in an array as a function of voltage and time.
Figure 10B:
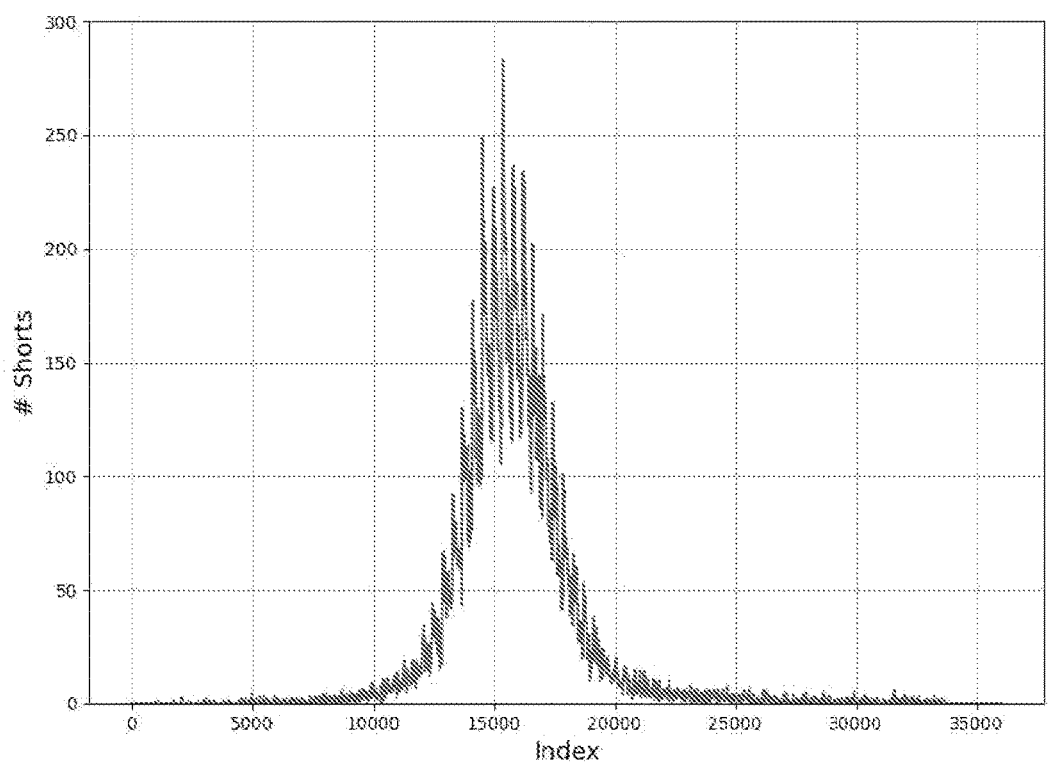
FIG. 10B illustrates a plot of the number of deactivations/shorts, which result from membrane disruption, as a function of voltage and time.

In some embodiments, the upper limit of the voltage waveform can be determined by comparing the kinetics and/or probability of pore insertion as a function of voltage and time to the kinetics and/or probability of membrane damage as a function of voltage and time. For example, FIG. 10A illustrates a plot of the number of pore insertions in an array as a function of voltage, and FIG. 10B illustrates a plot of the number of deactivations/shorts, which typically result from membrane disruption and damage, as a function of voltage. From these two plots, an optimal maximum voltage can be determined that balances a high number of pore insertions with a low number of deactivations/shorts.

In some embodiments, the concentration of pores in the solution during the pore insertion step is selected to be low enough to reduce passive insertion of pores into the membranes, while still being high enough to permit voltage assisted insertion of the pores into the membranes. Passive insertion of pores refers to the insertion of pores into the membrane without the application of voltage across the membrane to assist in pore insertion. In some embodiments, the percentage of pores inserted through passive insertion is less than 50%, 40%, 30%, 20%, or 10%, and the percentage of pores inserted through voltage assisted insertion is at least 50%, 60%, 70%, 80%, or 90%. Reducing the rate of passive pore insertion may reduce the likelihood of multiple pores being inserted into a single membrane.

In some embodiments, leakage current can cause a buildup of voltage in one or more cells in the array once a membrane is placed over the cells. This trapped charge can vary in magnitude over time and between cells, making it difficult to apply a uniform voltage across all the membranes of the cells when inducing poration. For example, applying a uniform voltage (Vapp) to all the cells when varying amounts of trapped charge are present in the cells in the array, can result in the cells experiencing different amounts of effective voltage during the poration step, which can lead to high levels of variability in the numbers of cells with single pore insertion and/or excessive amounts of voltage being applied in some cells which can cause damage to the membrane. Using a stepped or ramped voltage waveform can solve these problems.

In some embodiments, the formation of the membrane over the opening of the cell is accomplished by flowing a solvent and membrane material, such as a lipid or block copolymer, over the opening of the cell. Then, if a lipid is used for example, the membrane can be thinned into a bilayer by applying a voltage across the membrane, as further described in U.S. Patent Publication No. 20170283867A1, and/or by manipulating the osmolarity imbalance across the membrane as further described in International Patent Publication No. WO2018001925, each of which is herein incorporated by reference in its entirety for all purposes. As described herein, a thinned membrane is a membrane that is sufficiently thinned (i.e., thickness less than length of pore, for example) such that a pore can be inserted into the membrane, while an unthinned membrane is a membrane having a thickness that is too large (i.e., thickness greater than length of pore, for example) to permit insertion of the pore. In some embodiments, the formation of the thinned membrane (i.e., lipid bilayers) over the cells in the array can be completed before starting the poration process and inserting the pores into the membranes. In other embodiments, the process of thinning the membrane can be combined with the process of inserting the pore into the membrane by, for example, using the same voltage waveform, such as any of the voltage waveforms described herein, for both the thinning process and the poration process, and the pore complex can be flowed over the membrane during the combined thinning and poration process. In some embodiments, the combined thinning and poration process can be applied after the membrane material has already been dispensed over the cells and formed unthinned membranes across the cells in the array because applying voltage during membrane material dispense and the formation of the initial unthinned membrane may trap charge unevenly. In addition, an osmotic imbalance can be established across the membrane during the combined thinning and poration process. Combining the thinning and poration steps can substantially reduce the time it takes to prepare the pore sensors in the array, thereby improving the throughput of the sensor array system.

The methods described herein provide numerous benefits, including improving the rate of successful single pore insertion, reducing the rate of multiple pore insertions, and reducing the likelihood of damaging the membrane.

IV. Self-Limiting Pore Insertion in Faradaic Systems and Methods

As described above, in systems and methods where the voltage application is capacitively coupled, such as non-faradaic electrochemical systems, the voltage that drives pore insertion decays at a rate proportional to the membrane conductance. Thus when the conductance is increased by several orders of magnitude (e.g., sealed membrane to singly porated membrane), the voltage that is maintained across the membrane is rapidly diminished and remains low for subsequent voltage application without the need to alter the voltage applied to porated membranes. In this way, an array of electrodes with suspended membranes can be used to drive self-limiting pore insertion under a variety of conditions without active stimulus change intended to prevent additional pores inserting.

However, in systems where the voltage application is resistively coupled, e.g. faradaic electrochemical systems, the voltage across the membrane does not decay as a first order effect of conductance change of the membrane. As long as the resistive coupling between electrode and electrolyte is maintained, the voltage on the membrane is to first order constant. By initially dispensing a fluid that is capable of resistive coupling, yet in a state that prevents such, a capacitive coupling can be temporarily and reversibly established to enable self-limiting poration. After pore insertion, the fluid can be modified through exchange of solution or voltage application to again allow for resistive coupling.

For example, a reversible electrochemical system A+e=B, where "e" is an electron and A and B are oxidized states of a chemical species, could be prevented from proceeding forward by eliminating all of species "A" initially so that the solution only contains species "B". In such a condition, the system would behave as capacitively coupled under negative (reducing) voltage bias. By applying a positive (oxidizing) voltage bias, species A may be regenerated and the system will regain its faradaic (resistively coupled) properties.

Similarly, if species "B" is eliminated instead so that the solution only contains species "A", the solution would behave as capacitively coupled under positive (oxidizing) voltage bias. By applying a negative (reducing) voltage bias, species "B" would be regenerated and the system will regain its faradaic (resistively coupled) properties.

This allows the system and method to be selectively and reversibly operated as either a faradaic or non-faradaic system and method, as desired. As described herein, temporary or selective operation as a non-faradaic system allows the self-limiting pore insertion systems and methods to be utilized. For example, a ramped voltage waveform can be applied to facilitate single pore insertion, and after the pore solution is removed and replaced by a solution containing the sample with the molecule to be sequence, the system and method can be operated under faradaic conditions as described above, by for example, providing only one half of a oxidized and reduced species pair and operating under the appropriate oxidizing or reducing conditions.

In some embodiments, the solution containing the pores that is used during pore insertion does not include a redox couple or pair (i.e., neither "A" or "B", or just one of "A" or "B"). In some embodiments, the solution containing the molecule to be sequenced (i.e., a nucleic acid, a polymer, a derivative molecule of a nucleic acid, etc.) may contain the redox couple or pair, or may contain one of the species of the redox couple. In some embodiments, a voltage is used to regenerate the missing species of the redox couple.

Examples of redox couples include ferrocyanide and ferricyanide, ferrocene carboxylic acid (FCA) and ferrocene acetic acid (FAA), $[Co(bpy)]^{2+/3+}$, and other water soluble redox couples.

A. Sequencing Systems and Methods Particularly Suitable for Use with Faradaic Conditions.

In some sequencing systems, particularly where large molecules are threaded through the pore, operation under faradaic conditions can be desirable because it can allow for constant application of voltage across the pore to drive the molecule through the pore and/or for the acquisition of continuous measurement readings over long durations. Examples of nanopore sequencing systems and methods that thread the sample molecule through the pore during sequencing include sequencers from Oxford Nanopore (i.e. U.S. Pat. Nos. 9,758,823 and 10,416,117, each of which is incorporated by reference in its entirety) and Stratos Genomics (i.e. U.S. Pat. Nos. 7,939,259 and 9,771,614, each of which is incorporated by reference in its entirety).

For example, Stratos Genomics sequences nucleic acids by creating an "Xpandomer" from a nucleic acid template. This is achieved by encoding the nucleic acid information on a surrogate polymer of extended length which is easier to detect. The surrogate polymer (referred to herein as an "Xpandomer") is formed by template directed synthesis which preserves the original genetic information of the target nucleic acid, while also increasing linear separation of the individual elements of the sequence data.

In one embodiment, a method is disclosed for sequencing a target nucleic acid, comprising: a) providing a daughter strand produced by a template-directed synthesis, the daughter strand comprising a plurality of subunits coupled in a sequence corresponding to a contiguous nucleotide sequence of all or a portion of the target nucleic acid, wherein the individual subunits comprise a tether, at least one probe or nucleobase residue, and at least one selectively cleavable bond; b) cleaving the at least one selectively cleavable bond to yield an Xpandomer of a length longer than the plurality of the subunits of the daughter strand, the Xpandomer comprising the tethers and reporter elements for parsing genetic information in a sequence corresponding to the contiguous nucleotide sequence of all or a portion of the target nucleic acid; and c) detecting the reporter elements of the Xpandomer.

In more specific embodiments, the reporter elements for parsing the genetic information may be associated with the tethers of the Xpandomer, with the daughter strand prior to cleavage of the at least one selectively cleavable bond, and/or with the Xpandomer after cleavage of the at least one selectively cleavable bond. The Xpandomer may further comprise all or a portion of the at least one probe or nucleobase residue, and the reporter elements for parsing the genetic information may be associated with the at least one probe or nucleobase residue or may be the probe or nucleobase residues themselves. Further, the selectively cleavable bond may be a covalent bond, an intra-tether bond, a bond between or within probes or nucleobase residues of the daughter strand, and/or a bond between the probes or nucleobase residues of the daughter strand and a target template.

In further embodiments, oligomer substrate constructs for use in a template directed synthesis for sequencing a target nucleic acid are disclosed. Oligomer substrate constructs comprise a first probe moiety joined to a second probe moiety, each of the first and second probe moieties having an end group suitable for the template directed synthesis, and a tether having a first end and a second end with at least the first end of the tether joined to at least one of the first and second probe moieties, wherein the oligomer substrate construct when used in the template directed synthesis is capable of forming a daughter strand comprising a constrained Xpandomer and having a plurality of subunits coupled in a sequence corresponding to the contiguous nucleotide sequence of all or a portion of the target nucleic acid, wherein the individual subunits comprise a tether, the first and second probe moieties and at least one selectively cleavable bond.

In another embodiment, monomer substrate constructs for use in a template directed synthesis for sequencing a target nucleic acid are disclosed. Monomer substrate constructs comprise a nucleobase residue with end groups suitable for the template directed synthesis, and a tether having a first end and a second end with at least the first end of the tether joined to the nucleobase residue, wherein the monomer substrate construct when used in the template directed synthesis is capable of forming a daughter strand comprising a constrained Xpandomer and having a plurality of subunits coupled in a sequence corresponding to the contiguous nucleotide sequence of all or a portion of the target nucleic acid, wherein the individual subunits comprise a tether, the nucleobase residue and at least one selectively cleavable bond.

In yet further embodiments, template-daughter strand duplexes are disclosed comprising a daughter strand duplexed with a template strand, as well as to methods for forming the same from the template strand and the oligomer or monomer substrate constructs.

V. Ac Modulation of Voltage Waveform

In some embodiments, as shown in FIG. 7, the pore insertion waveform 700 can be a voltage waveform with AC modulation. As shown, the pore insertion waveform 702 is stepped, and the AC modulation 702 component can be overlaid on top of the voltage waveform 700 to provide rapid voltage fluctuations at each stepped voltage. The voltage fluctuations or changes allow electrical measurements to be taken while the pore insertion waveform 700 is being applied during the electroporation step during pore insertion. These electrical measurements can be used to check membrane integrity (i.e., detect membrane failure as a short condition), membrane leakiness (i.e., membrane resistance and/or conductance), insertion of a pore, and generally can be used to monitor the progress of the electroporation step. In some embodiments, measurements cannot be taken while the voltage waveform is being applied, and in those embodiments, measurements are generally taken before, after, or between applications of the voltage waveforms. Overlaying the AC modulation component to a voltage waveform allows for the simultaneous application of the voltage waveform and the taking of measurements.

In some embodiments, other voltage waveforms can also be overlaid with an AC modulation component. For example, a membrane formation waveform can be AC modulated to allow for electrical measurements to be taken while the membrane formation waveform is applied during the step of forming the membrane over the well. These electrical measurements can be used to whether the well is covered with a membrane forming material (i.e., checking for a short condition), check membrane integrity (i.e., detect membrane failure as a short condition), membrane leakiness (i.e., membrane resistance and/or conductance), whether the membrane is of a thickness suitable for pore insertion, and generally can be used to monitor the progress of the membrane formation step.

In some embodiments, another voltage waveform that can be AC modulated is a translocation voltage waveform that can be used to translocate a molecule through the pore.

In some embodiments, the amplitude of the AC modulation component can be minimized in order to reduce the affect of the AC modulation component on the primary function of the voltage waveform (i.e., membrane formation or pore insertion), while still allowing accurate measurements to be obtained. A relatively large amplitude AC modulation component may significantly subject the membrane to higher than expected transient voltages during the membrane formation step and/or the pore insertion step, which can result in membrane failure or multiporation, for example. Therefore, in some embodiments, the amplitude of the AC modulation component may be less than 200, 190, 180, 170, 160, 150, 140, 130, 120, 110, 100, 90, 80, 70, 60, 50, 40, 30, 20, or 10 mV. In some embodiments, the amplitude of the AC modulation component may be less than 50, 40, 30, 20, or 10% of the amplitude of the voltage waveform being modulated. In other embodiments, the amplitude of the AC modulation component can scale with the amplitude of the voltage waveform being modulated.

In some embodiments, the frequency of the AC modulation component can be minimized while still allowing for accurate measurements. In some embodiments, the frequency of the AC modulation can be less than 10, 9, 8, 7, 6, 5, 4, 3, 2, 1, 0.5, 0.1 times the sampling maximum frequency. In some embodiments, the frequency is at least 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000 Hz. In some embodiments, the frequency is less than 1000, 900, 800, 700, 600, 500, 400, 300, 200, 100, 90, 80, 70, 60, 50, 40, 30, 20, or 10 Hz. In some embodiments, the frequency is between 10 to 1000 Hz, or 25 to 750 Hz, or 50 to 500 Hz.

Figure 8B:
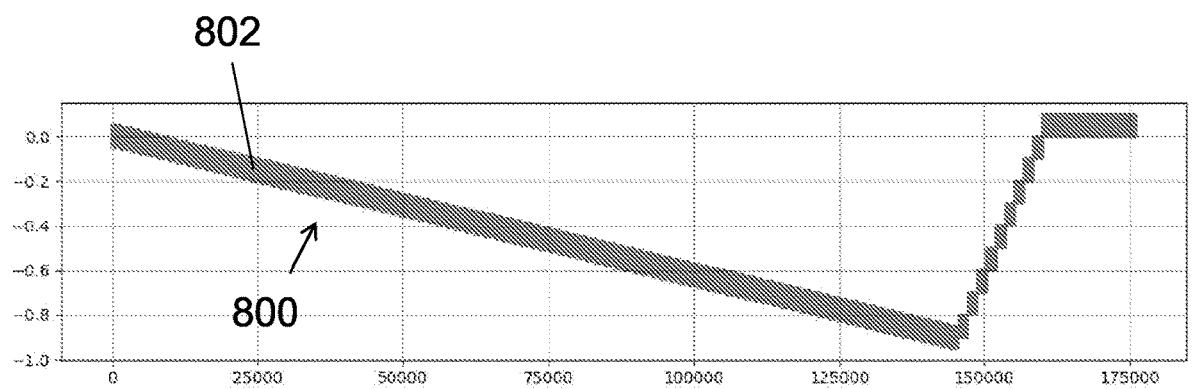

FIG. 8B illustrates an embodiment of the self-limiting poration waveform that is shown in FIG. 8A with the addition of an AC modulation component 802 for making measurements. In this embodiment, the amplitude of the AC modulation component is 100 mV and is shown as the thickness of the line on the graph.

Any other voltage waveform can be overlaid with an AC modulation component in order to allow for measurements to be taken while the voltage waveform is applied.

VI. Computer System

Any of the computer systems mentioned herein can utilize any suitable number of subsystems, many of which may be optional. Examples of such subsystems are shown in FIG. 11 in computer system 1110. In some embodiments, a computer system includes a single computer apparatus, where the subsystems can be the components of the computer apparatus. In other embodiments, a computer system includes multiple computer apparatuses, each being a subsystem, with internal components. A computer system can include desktop and laptop computers, tablets, mobile phones, and other mobile devices.

The subsystems shown in FIG. 11 are interconnected via a system bus 1180. Additional subsystems such as a printer 1174, keyboard 1178, storage device(s) 1179, monitor 1176 which is coupled to display adapter 1182, and others are shown. Peripherals and input/output (I/O) devices, which couple to I/O controller 1171, can be connected to the computer system by any number of means known in the art such as I/O port 1177 (e.g., USB, FireWire®). For example, I/O port 1177 or external interface 1181 (e.g. Ethernet, Wi-Fi, etc.) can be used to connect computer system 1110 to a wide area network such as the Internet, a mouse input device, or a scanner. The interconnection via system bus 1180 allows the central processor 1173 to communicate with each subsystem and to control the execution of a plurality of instructions from system memory 1172 or the storage device(s) 1179 (e.g., a fixed disk, such as a hard drive, or optical disk), as well as the exchange of information between subsystems. The system memory 1172 and/or the storage device(s) 1179 can embody a computer readable medium. Another subsystem is a data collection device 1175, such as a camera, microphone, accelerometer, or other sensor and the like. Any of the data mentioned herein can be output from one component to another component and can be output to the user.

A computer system can include a plurality of the same components or subsystems, e.g., connected together by external interface 1181, by an internal interface, or via removable storage devices that can be connected and removed from one component to another component. In some embodiments, computer systems, subsystem, or apparatuses communicate over a network. In such instances, one computer can be considered a client and another computer a server, where each can be part of a same computer system. A client and a server can each include multiple systems, subsystems, or components.

Aspects of embodiments can be implemented in the form of control logic using hardware circuitry (e.g. an APSIC or FPGA) and/or using computer software with a generally programmable processor in a modular or integrated manner. As used herein, a processor can include a single-core processor, multi-core processor on a same integrated chip, or multiple processing units on a single circuit board or networked, as well as dedicated hardware. Based on the disclosure and teachings provided herein, a person of ordinary skill in the art will know and appreciate other ways and/or methods to implement embodiments of the present invention using hardware and a combination of hardware and software.

Any of the software components or functions described in this application can be implemented as software code to be executed by a processor using any suitable computer language such as, for example, Java, C, C++, C#, Objective-C, Swift, or scripting language such as Perl or Python using, for example, conventional or object-oriented techniques. The software code can be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium can be any combination of such storage or transmission devices.

Such programs can also be encoded and transmitted using carrier signals adapted for transmission via wired, optical, and/or wireless networks conforming to a variety of protocols, including the Internet. As such, a computer readable medium can be created using a data signal encoded with such programs. Computer readable media encoded with the program code can be packaged with a compatible device or provided separately from other devices (e.g., via Internet download). Any such computer readable medium can reside on or within a single computer product (e.g. a hard drive, a CD, or an entire computer system), and can be present on or within different computer products within a system or network. A computer system can include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective step or a respective group of steps. Although presented as numbered steps, steps of methods herein can be performed at a same time or at different times or in a different order. Additionally, portions of these steps can be used with portions of other steps from other methods. Also, all or portions of a step can be optional. Additionally, any of the steps of any of the methods can be performed with modules, units, circuits, or other means of a system for performing these steps.

The specific details of particular embodiments can be combined in any suitable manner without departing from the spirit and scope of embodiments of the invention. However, other embodiments of the invention can be directed to specific embodiments relating to each individual aspect, or specific combinations of these individual aspects.

Although the foregoing embodiments have been described in some detail for purposes of clarity of understanding, the invention is not limited to the details provided. There are many alternative ways of implementing the invention. The disclosed embodiments are illustrative and not restrictive. The above description of example embodiments of the invention has been presented for the purposes of illustration and description. It is not intended to be exhaustive or to limit the invention to the precise form described, and many modifications and variations are possible in light of the teaching above.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

All patents, patent applications, publications, and descriptions mentioned herein are incorporated by reference in their entirety for all purposes. None is admitted to be prior art.

What is claimed is:

1. A method of forming an array of nanopore sensor cells, the method comprising:
    introducing a nanopore proximate to a cell in a solution comprising a first species of a redox couple but not a second species of the redox couple, the cell having a working electrode and a membrane sealing the cell, wherein the working electrode is powered by an electrically coupled power source;
    applying a first voltage waveform across the membrane of the cell, wherein the voltage waveform starts at first voltage and increases in magnitude over a period of time to a second voltage, wherein the first voltage waveform has a polarity that maintains the first species of the redox couple in its current oxidation state;
    inserting the nanopore into the membrane during the step of applying the first voltage waveform; and
    applying a second voltage waveform having a polarity that oxidizes or reduces the first species to the second species.

2. The method of claim 1, wherein the redox couple is water soluble.

3. The method of claim 1, wherein the redox couple is ferricyanide and ferrocyanide.

4. The method of claim 1, further comprising:
    threading a molecule through the nanopore; and
    applying a sequencing voltage to sequence the molecule under faradaic conditions.

5. A system for sequencing a molecule, the system comprising:
    an array of cells on a substrate, each cell having a working electrode and an opening configured to be sealed by a membrane with a nanopore;
    a counter electrode;
    a power source, wherein the power source is electrically coupled to each working electrode;
    a controller programmed to:
        deliver a first voltage waveform to the cell using the working electrode and the counter electrode, wherein (i) the first voltage waveform starts at first voltage and increases in magnitude over a period of time to a second voltage, wherein ii) the first voltage waveform has a polarity that maintains a first species of a redox couple in its current oxidation state, and wherein (iii) the controller is further programmed to deliver a second voltage waveform having a polarity that oxidizes or reduces the first species to the second species.

6. The system of claim 5, wherein the working electrode is configured to selectively operate as both a capacitively-coupled electrode and a resistively couple electrode.

7. The system of claim 5, further comprising a solution comprising the first species of the redox couple but not a second species of the redox couple, wherein the solution is configured to be disposed in the cells of the array.

8. The system of claim 7, wherein the redox couple is water soluble.

9. The system of claim 7, wherein the redox couple is ferricyanide and ferrocyanide.

10. The system of claim 5, wherein the controller is further programmed to:
apply a voltage to thread a molecule through the pore; and
apply a sequencing voltage to sequence the molecule under faradaic conditions.

11. A system for sequencing a molecule, the system comprising:
an array of cells on a substrate, each cell having a working electrode and an opening configured to be sealed by a membrane with a nanopore, wherein the working electrode is configured to selectively operate as both a capacitively-coupled electrode and a resistively couple electrode;
a counter electrode;
a power source, wherein the power source is electrically coupled to each working electrode;
a controller programmed to:
deliver a voltage waveform to the cell using the working electrode and the counter electrode, wherein the voltage waveform starts at first voltage and increases in magnitude over a period of time to a second voltage, wherein the voltage waveform has a polarity that maintains a first species of a redox couple in its current oxidation state.

12. The system of claim 11, wherein the controller is further programmed to deliver a second voltage waveform having a polarity that oxidizes or reduces the first species to the second species.

13. The system of claim 11, further comprising a solution comprising the first species of the redox couple but not a second species of the redox couple, wherein the solution is configured to be disposed in the cells of the array.

14. The system of claim 13, wherein the redox couple is water soluble.

15. The system of claim 13, wherein the redox couple is ferricyanide and ferrocyanide.

16. The system of claim 11, wherein the controller is further programmed to:
apply a voltage to thread a molecule through the pore; and
apply a sequencing voltage to sequence the molecule under faradaic conditions.

17. A system for sequencing a molecule, the system comprising:
an array of cells on a substrate, each cell having a working electrode and an opening configured to be sealed by a membrane with a nanopore;
a counter electrode;
a power source, wherein the power source is electrically coupled to each working electrode;
a controller programmed to:
deliver a voltage waveform to the cell using the working electrode and the counter electrode,
apply a voltage to thread a molecule through the pore, and
apply a sequencing voltage to sequence the molecule under faradaic conditions,
wherein the voltage waveform starts at first voltage and increases in magnitude over a period of time to a second voltage and wherein the voltage waveform has a polarity that maintains a first species of a redox couple in its current oxidation state.

18. The system of claim 17, wherein the working electrode is configured to selectively operate as both a capacitively-coupled electrode and a resistively couple electrode.

19. The system of claim 17, wherein the controller is further programmed to deliver a second voltage waveform having a polarity that oxidizes or reduces the first species to the second species.

20. The system of claim 17, further comprising a solution comprising the first species of the redox couple but not a second species of the redox couple, wherein the solution is configured to be disposed in the cells of the array.

21. The system of claim 20, wherein the redox couple is water soluble.

22. The system of claim 20, wherein the redox couple is ferricyanide and ferrocyanide.

23. A method of forming an array of nanopore sensor cells, the method comprising:
introducing a nanopore proximate to a cell in a solution comprising a first species of a redox couple but not a second species of the redox couple, the cell having a working electrode and a membrane sealing the cell, wherein the working electrode is powered by an electrically coupled power source;
applying a voltage waveform across the membrane of the cell, wherein the voltage waveform starts at first voltage and increases in magnitude over a period of time to a second voltage, wherein the voltage waveform has a polarity that maintains the first species of the redox couple in its current oxidation state;
inserting the nanopore into the membrane during the step of applying the voltage waveform;
threading a molecule through the nanopore; and
applying a sequencing voltage to sequence the molecule under faradaic conditions.

24. The method of claim 23, wherein the redox couple is water soluble.

25. The method of claim 23, wherein the redox couple is ferricyanide and ferrocyanide.

26. The method of claim 23, further comprising applying a second voltage waveform having a polarity that oxidizes or reduces the first species to the second species.

27. A method of forming an array of nanopore sensor cells, the method comprising:
introducing a nanopore proximate to a cell in a solution comprising a first species of a redox couple but not a second species of the redox couple, the cell having a working electrode and a membrane sealing the cell, wherein the working electrode is powered by an electrically coupled power source and wherein the working electrode is configured to selectively operate as both a capacitively-coupled electrode and a resistively couple electrode;
applying a voltage waveform across the membrane of the cell, wherein the voltage waveform starts at first voltage and increases in magnitude over a period of time to a second voltage, wherein the voltage waveform has a polarity that maintains the first species of the redox couple in its current oxidation state; and
inserting the nanopore into the membrane during the step of applying the voltage waveform.

28. The method of claim 27, wherein the redox couple is water soluble.

29. The method of claim 27, wherein the redox couple is ferricyanide and ferrocyanide.

30. The method of claim 27, further comprising applying a second voltage waveform having a polarity that oxidizes or reduces the first species to the second species.

31. The method of claim 30, further comprising:
threading a molecule through the nanopore; and
applying a sequencing voltage to sequence the molecule under faradaic conditions.

\* \* \* \* \*